US012690973B2

(12) United States Patent
Ginn

(10) Patent No.: US 12,690,973 B2
(45) Date of Patent: Jul. 28, 2026

(54) METHODS AND PROSTHESES FOR STABILIZING BONE STRUCTURES

(71) Applicant: Tenon Medical, Inc., Los Gatos, CA (US)

(72) Inventor: Richard S Ginn, Gilroy, CA (US)

(73) Assignee: Tenon Medical, Inc., Los Gatos, CA (US)

( * ) Notice: Subject to any disclaimer, the term of this patent is extended or adjusted under 35 U.S.C. 154(b) by 1087 days.

(21) Appl. No.: 17/834,392

(22) Filed: Jun. 7, 2022

(65) Prior Publication Data

US 2022/0296378 A1 Sep. 22, 2022

Related U.S. Application Data

(63) Continuation-in-part of application No. 17/469,132, filed on Sep. 8, 2021, now Pat. No. 12,115,076, which
(Continued)

(51) Int. Cl.
| | |
|---|---|
| *A61F 2/30* | (2006.01) |
| *A61B 5/055* | (2006.01) |
| *A61B 5/06* | (2006.01) |
| *A61B 6/00* | (2006.01) |
| *A61B 6/03* | (2006.01) |

(Continued)

(52) U.S. Cl.
CPC .......... *A61F 2/30988* (2013.01); *A61B 5/055* (2013.01); *A61B 5/062* (2013.01); *A61B 6/032* (2013.01); *A61B 6/485* (2013.01); *A61B 8/0841* (2013.01); *A61B 17/1604* (2013.01); *A61B 17/1664* (2013.01); *A61B 17/1671*

(2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01);
(Continued)

(58) Field of Classification Search
CPC ....... A61F 2/30988; A61F 2002/30995; A61B 2017/681; A61B 17/863; A61B 17/7055; A61B 17/8685; A61B 17/1757; A61B 17/683
See application file for complete search history.

(56) References Cited

U.S. PATENT DOCUMENTS

| | | | | |
|---|---|---|---|---|
| 4,723,541 A | * | 2/1988 | Reese ................... | A61B 17/72 606/916 |
| 6,319,254 B1 | * | 11/2001 | Giet ................... | A61B 17/8875 606/104 |

(Continued)

*Primary Examiner* — Lynnsy M Summitt
(74) *Attorney, Agent, or Firm* — Francis Law Group

(57) ABSTRACT

Methods are described for stabilizing dysfunctional bone structures. The methods include the step of providing prostheses having an elongated body with dual, i.e., first and second, threaded ends and an intervening central region. The threaded ends have helical threads wound thereon that extend from the intervening central region to the ends of the first and second threaded ends. The methods further include the steps of creating a pilot opening in the dysfunctional bone structures and inserting the prostheses into the pilot opening and, thereby dysfunctional bone structure.

10 Claims, 28 Drawing Sheets

Related U.S. Application Data is a continuation of application No. 17/463,831, filed on Sep. 1, 2021, now Pat. No. 12,409,039, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | |
|---|---|
| *A61B 8/08* | (2006.01) |
| *A61B 17/16* | (2006.01) |
| *A61B 17/70* | (2006.01) |
| *A61B 17/88* | (2006.01) |
| *A61B 34/20* | (2016.01) |
| *A61F 2/44* | (2006.01) |
| *A61F 2/46* | (2006.01) |

(52) U.S. Cl.
CPC .............. *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 7,491,236 | B2 * | 2/2009 | Cragg .................... | A61F 2/441 606/301 |
| 7,608,097 | B2 * | 10/2009 | Kyle .................... | A61B 17/864 606/93 |
| 8,945,193 | B2 * | 2/2015 | Kirschman ........ | A61B 17/8841 606/317 |
| 8,974,508 | B2 * | 3/2015 | Stephan ................ | A61B 17/84 606/313 |
| 9,687,256 | B2 * | 6/2017 | Granberry .......... | A61B 17/1682 |
| 9,820,788 | B2 * | 11/2017 | Vrionis ............. | A61B 17/8685 |
| 9,974,573 | B2 * | 5/2018 | Schell ................ | A61B 17/1671 |
| 10,064,670 | B2 * | 9/2018 | Mootien ............ | A61B 17/844 |
| 10,799,367 | B2 * | 10/2020 | Vrionis ................ | A61B 17/70 |
| 10,932,838 | B2 * | 3/2021 | Mehl ................ | A61B 17/8685 |
| 10,940,008 | B2 * | 3/2021 | Patel .................. | A61F 2/30771 |
| 11,234,746 | B2 * | 2/2022 | Peterson ............. | A61B 17/863 |
| 11,571,245 | B2 * | 2/2023 | Stuart ................ | A61B 17/864 |
| 11,712,276 | B2 * | 8/2023 | Ek .......................... | A61B 17/84 606/328 |
| 11,883,296 | B2 * | 1/2024 | Morgenstern Lopez ................... | A61F 2/28 |
| 2013/0238036 | A1 * | 9/2013 | Sinha .................... | A61B 17/68 606/317 |
| 2014/0066758 | A1 * | 3/2014 | Marik ................ | A61B 17/7064 600/431 |
| 2014/0330370 | A1 * | 11/2014 | Matheny .............. | A61F 2/2418 623/2.37 |
| 2016/0220291 | A1 * | 8/2016 | Russell ............. | A61B 17/8811 |
| 2016/0287300 | A1 * | 10/2016 | Mccormick ........ | A61B 17/7291 |
| 2016/0310188 | A1 * | 10/2016 | Marino .................... | A61F 2/28 |
| 2018/0050128 | A1 * | 2/2018 | Gabriele ............... | A61L 26/008 |
| 2018/0325676 | A1 * | 11/2018 | Donner ............. | A61B 17/1739 |
| 2023/0301665 | A1 * | 9/2023 | Aksu ..................... | A61B 17/17 |

* cited by examiner

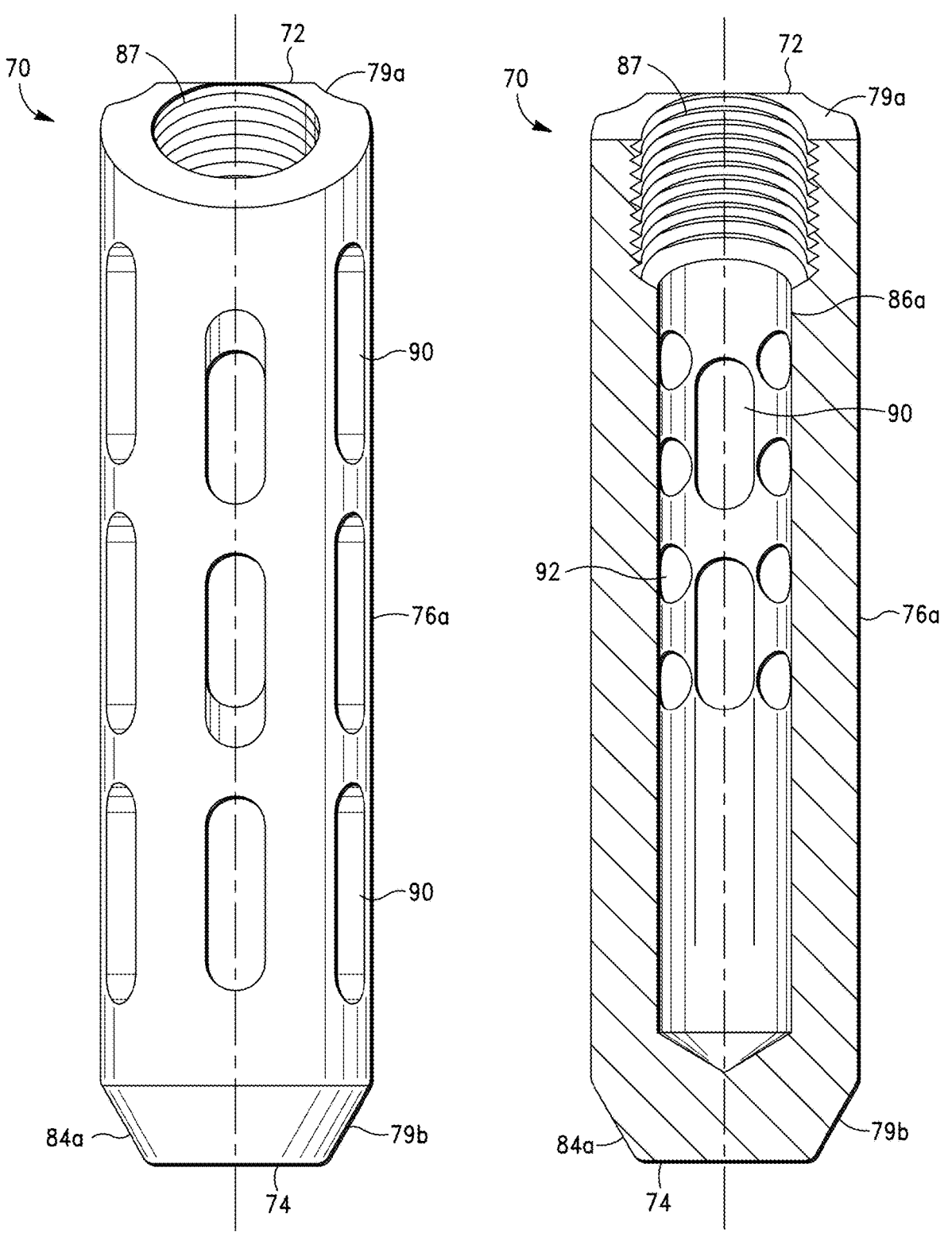
*FIG. 5G*              *FIG. 5H*

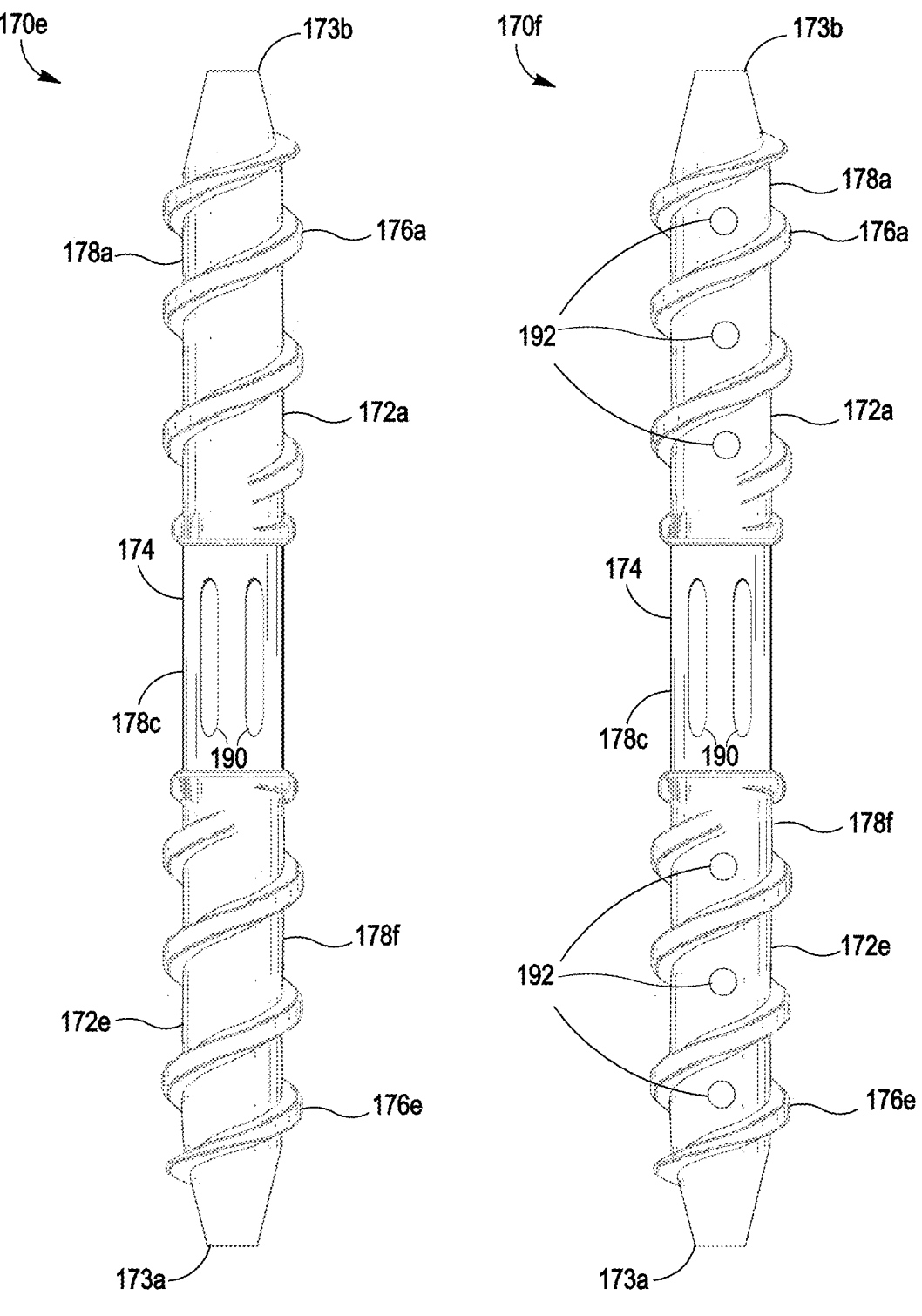
*FIG. 8F*    *FIG. 8G*

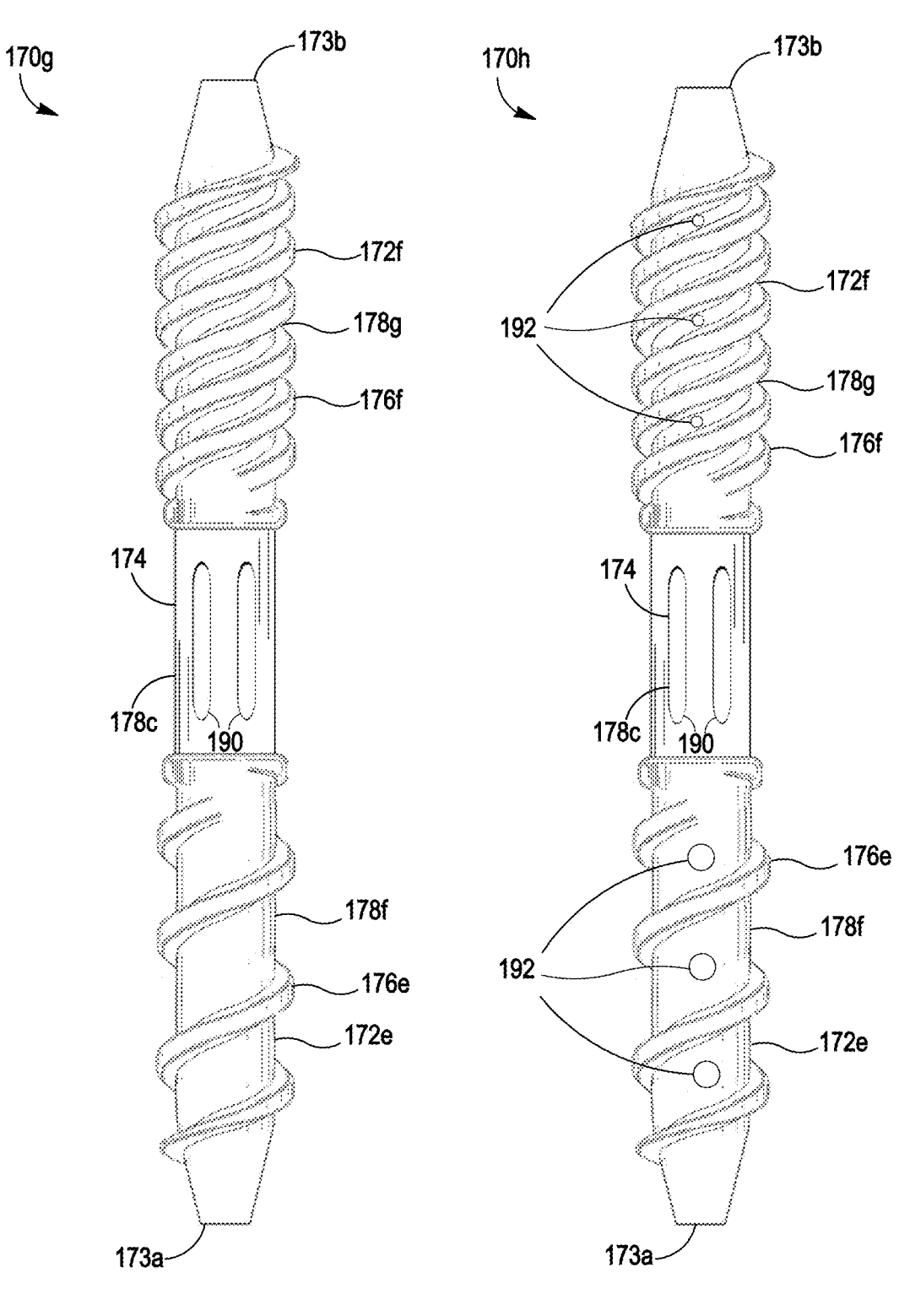
*FIG. 8H*                    *FIG. 8I*

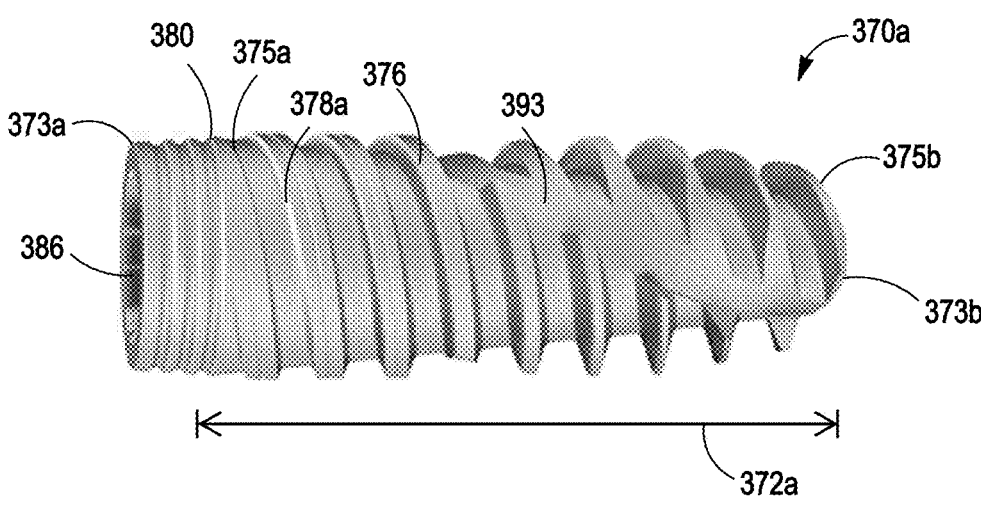
**Fig. *10A***
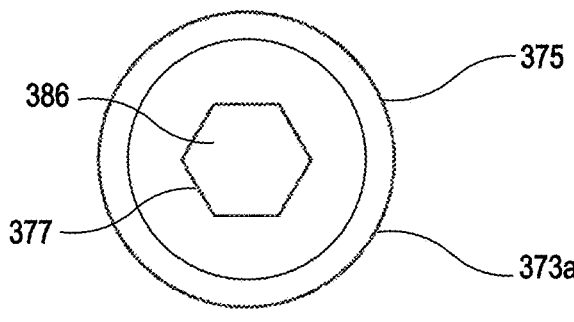
**Fig. *10B***
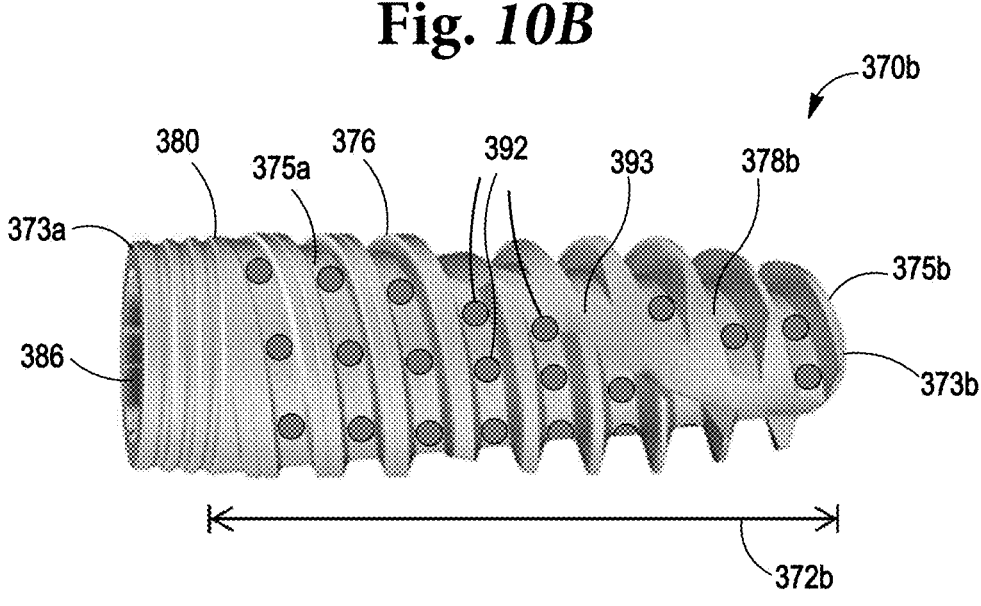
**Fig. *10C***

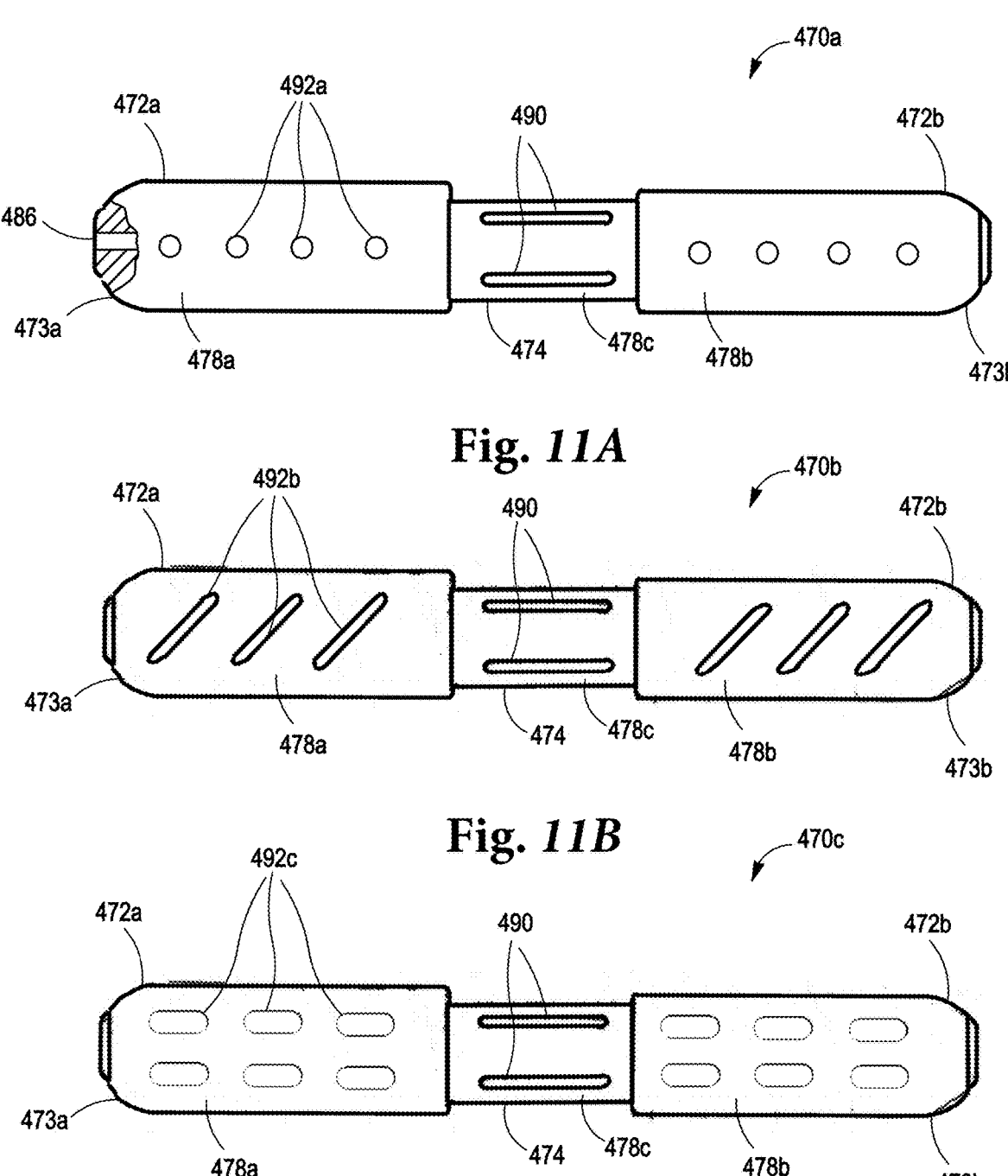
Fig. *11A*
Fig. *11B*
Fig. *11C*

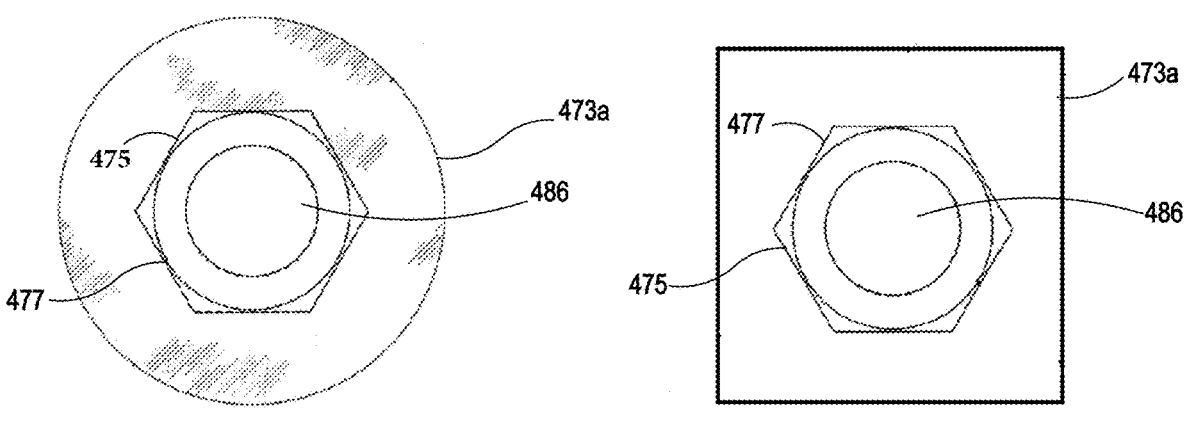
Fig. *11D*                    Fig. *11E*
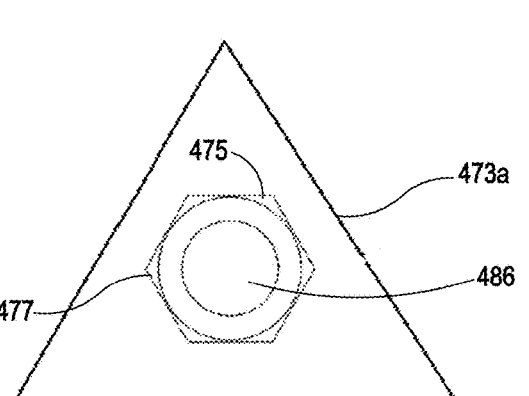
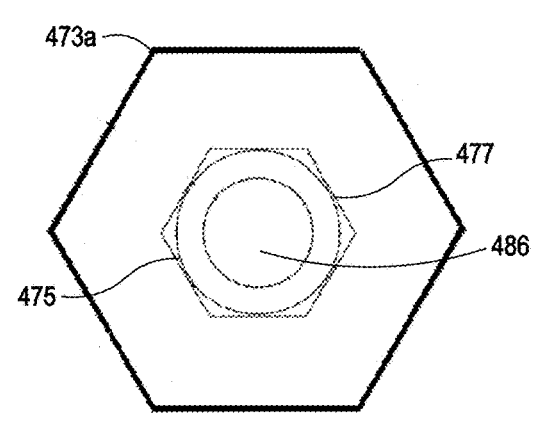
Fig. *11F*                    Fig. *11G*
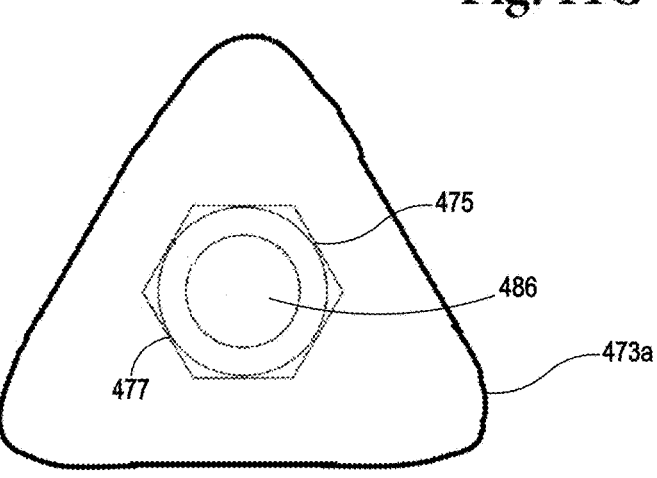
Fig. *11H*

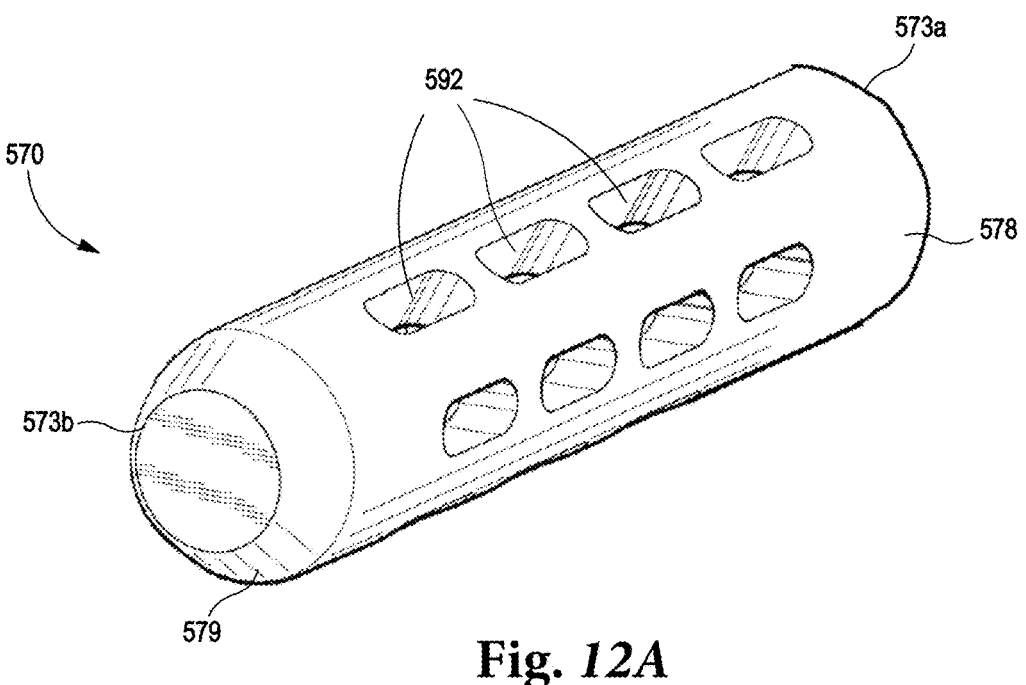
**Fig. *12A***
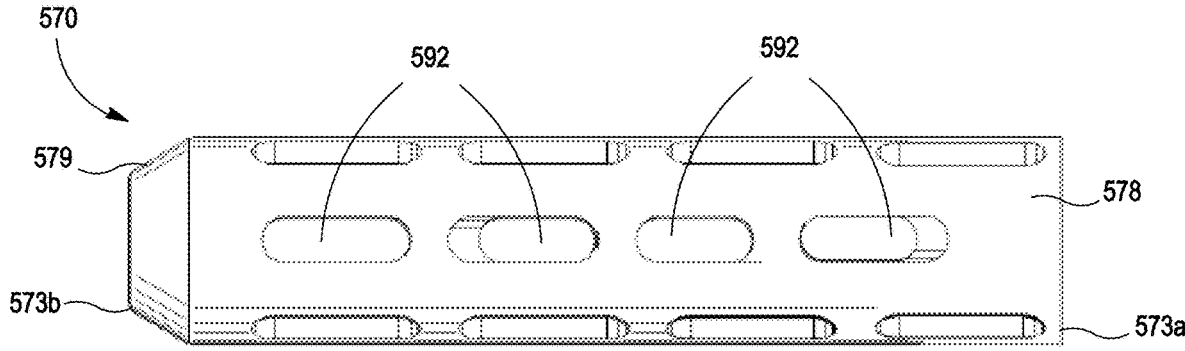
**Fig. *12B***
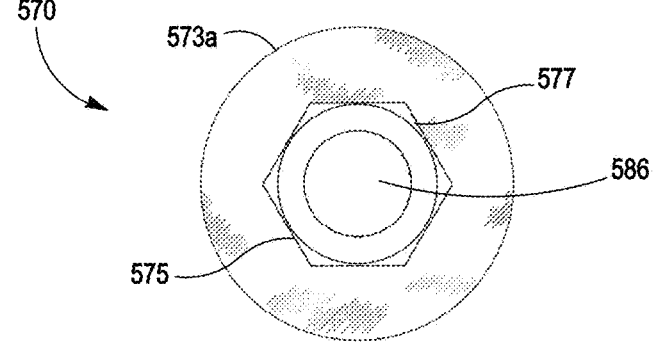
**Fig. *12C***

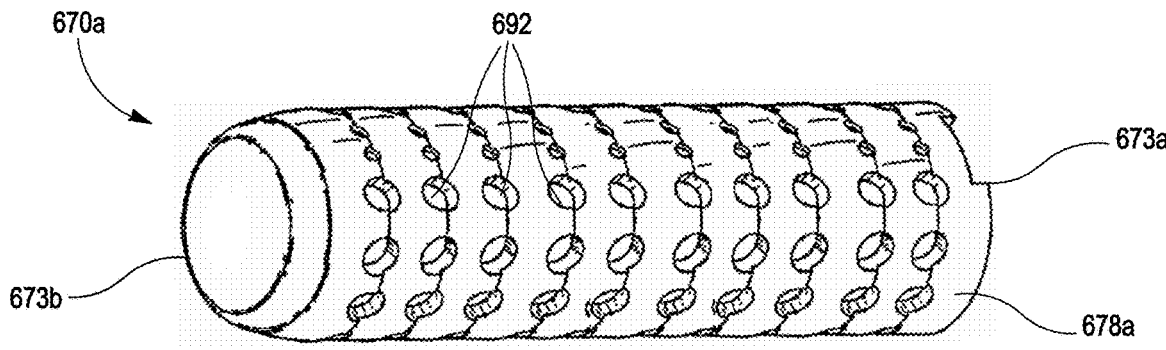
**Fig. *13A***
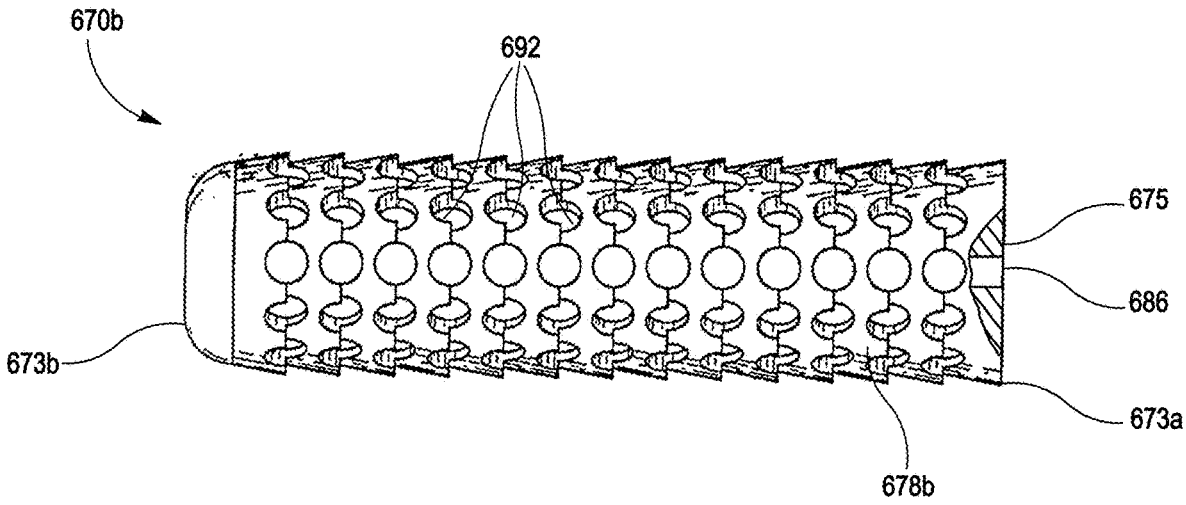
**Fig. *13B***

METHODS AND PROSTHESES FOR STABILIZING BONE STRUCTURES

CROSS-REFERENCES TO RELATED APPLICATIONS

This application is a continuation-in-part of U.S. patent application Ser. No. 17/469,132, filed on Sep. 8, 2021, which is a continuation of U.S. patent application Ser. No. 17/463, 831, filed Sep. 1, 2021, which is a continuation-in-part application of U.S. patent application Ser. No. 13/857,977, filed Apr. 5, 2013, now U.S. Pat. No. 11,273,042, which is a continuation application of U.S. patent application Ser. No. 13/192,289, filed Jul. 27, 2011, now abandoned, which claims the benefit of U.S. provisional patent application Ser. No. 61/368,233, filed Jul. 27, 2010.

FIELD OF THE INVENTION

The present invention relates to methods and apparatus for stabilizing bone structures, including articulating bone structures, such a sacroiliac (SI) joints and intervertebral joints.

BACKGROUND OF THE INVENTION

As is well known in the art, there are a multitude of skeletal disorders that often necessitate stabilizing bone structures, such as skeletal member, i.e., bone, fractures and dysfunctional non-articulating and articulating bone structures, i.e., joints, such as synovial joint degeneration, and like disorders.

Various prostheses have thus been developed to stabilize bone structures. As is also well known in the art, the most common type of prostheses that have been employed to stabilize damaged or diseased and, hence, dysfunctional bone structures are bone screws and pins. The noted prostheses, which typically comprise a solid elongated structure, are often employed in combination with other fastening implements (e.g., bone plates).

More recently, considerable effort has been directed to developing improved threaded and non-threaded prostheses, i.e., screw and pin structures, and other prosthesis configurations for stabilizing bone structures; particularly, dysfunctional sacroiliac (SI) joints and intervertebral joints of the spine (e.g., adjacent vertebrae)

Referring now to FIG. 1, there is shown a schematic illustration of a human pelvic region showing the articulating bone structures, i.e., sacroiliac (SI) joints, thereof. As illustrated in FIG. 1, the SI joint 6 is defined by the interface between the articular surfaces of the sacrum 2 and the ilium 4. Thus, the SI joint 6 is defined by (and, hence, comprises) portions of the sacrum 2 and ilium 4.

Generally, the articular surfaces of the sacrum 2 and the ilium 4 that define the SI joint 6 comprise cortical bone 8, which is more compact, dense, and hard relative to softer trabecular bone 10, which, as further illustrated in FIG. 1, is disposed in the interior regions of the sacrum and ilium 2, 4.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

As is also well established, loads and, hence, forces exerted on the spine can similarly adversely affect the biomechanical functions of the spine, which can, and often will, result in intervertebral joint dysfunction.

Intervertebral joint dysfunction, and pain associated therewith, can be caused by various abnormalities and/or disorders, including herniated discs, traumatic fracture of the spine, degenerative disc disease, degenerative arthritis, and other degenerative conditions of intervertebral joint structures.

Various non-surgical methods, such as administration of pharmacological agents, e.g., the corticosteroid prednisone, have been developed and employed to treat SI and intervertebral joint dysfunction. However, such non-surgical methods have garnered limited success.

Considerable effort has thus recently been directed to developing improved surgical methods and apparatus, i.e., prostheses, to treat SI and intervertebral joint dysfunction. Such prostheses are typically configured and adapted to stabilize (i.e., reinforce or modulate articulation of) the dysfunctional bone structure, i.e., joint, via fixation or fusion of bones associated therewith.

Although several conventional surgical bone structure stabilization methods and associated bone prostheses have effectively ameliorated pain associated with bone structure dysfunction, there remains many disadvantages associated with the conventional methods and associated bone prostheses.

A major disadvantage associated with many conventional surgical bone structure stabilization methods is that the surgeon is typically required to make a substantial incision in and through the skin and tissues of a subject to access the dysfunctional bone structure. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive surgical methods to stabilize dysfunctional bone structures; particularly, SI and intervertebral joints, have thus been developed to address the noted disadvantages associated with open surgery methods. Although conventional minimally-invasive bone structure stabilization methods, such as the intervertebral bone structure (i.e., facet joint) stabilization methods disclosed in U.S. Pub. No. 2009/0076551 to Petersen, have garnered some success in relieving pain associated with bone structure, i.e., joint dysfunction and have effectively addressed many of the disadvantages associated with open surgery methods, there similarly remains many disadvantages associated with conventional minimally-invasive bone structure stabilization methods.

A major disadvantage associated with many conventional minimally-invasive bone structure stabilization methods and associated prostheses, such as the intervertebral bone structure stabilization methods and prostheses disclosed in U.S.

Pub. No. 2009/0076551 to Petersen, is that pre-existing bone structure abnormalities can lead to displacement of the implanted prostheses, which can, and often will result in damage to surrounding bone and soft tissue structures.

An additional disadvantage associated with many conventional minimally invasive bone structure stabilization methods is that the prostheses associated therewith are often prone to failure due to ineffective engagement of the prostheses to the dysfunctional bone structure, which can, and often will, result in displacement of the prostheses in the dysfunctional bone structure.

It would thus be desirable to provide improved bone structure stabilization methods and prostheses that substantially reduce or eliminate the disadvantages associated with conventional bone structure stabilization methods and prostheses.

It is therefore an object of the invention to provide improved bone structure stabilization methods and prostheses that substantially reduce or eliminate the disadvantages associated with conventional bone structure stabilization methods and prostheses.

It is another object of the invention to provide improved bone structure prostheses that can be readily employed to stabilize dysfunctional bone structures, including individual skeletal members and non-articulating and articulating bone structures; particularly, dysfunctional SI and intervertebral joints.

It is another object of the invention to provide improved bone structure prostheses, which, when implanted in a dysfunctional non-articulating or articulating bone structure, such as a dysfunctional SI or intervertebral joint, effectively ameliorate pain associated with bone structure dysfunction.

It is another object of the invention to provide improved bone structure prostheses that can readily be employed in minimally-invasive bone structure stabilization methods and provide secure engagement to bone structures.

It is another object of the invention to provide improved bone structure prostheses that possess optimal structural properties.

It is another object of the invention to provide improved bone structure prostheses that can be readily employed to stabilize individual bone structures, i.e., skeletal members, via fixation or fusion.

It is yet another object of the invention to provide improved bone structure prostheses that facilitate remodeling of damaged osseous tissue and regeneration of new osseous tissue and osseous tissue structures when engaged to bone structures.

SUMMARY OF THE INVENTION

The present invention is directed to methods and apparatus, i.e., prostheses, for stabilizing dysfunctional bone structures, including individual skeletal members, such as a tibia and femur, and non-articulating and articulating bone structures; particularly, dysfunctional SI and intervertebral joints.

In some embodiments of the invention, there are thus provided bone structure prostheses for stabilizing dysfunctional bone structures.

In one embodiment of the invention, the bone structure prosthesis comprises an elongated threaded member adapted to threadably engage bone structures, the elongated threaded member comprising a first threaded end, a second threaded end that is disposed opposite the first threaded end, and an intervening non-threaded central region that is disposed between the first threaded end and the second threaded end, the elongated threaded member further comprising a proximal end and a distal end disposed opposite the proximal end, the distal end comprising a closed configuration, the first threaded end comprising a first thread that extends from the non-threaded central region to the distal end of the first threaded end, the first thread disposed and positioned on the first threaded end in a substantially helical manner in a first direction, the second threaded end comprising a second thread that extends from the non-threaded central region to the proximal end of the second threaded end, the second thread disposed and positioned on the second threaded end in a substantially helical manner in a second direction, the elongated threaded member further comprising an internal lumen that extends longitudinally through the elongated threaded member, the elongated threaded member further comprising an osteogenic composition, the osteogenic composition disposed in the internal lumen, the non-threaded central region of the elongated threaded member comprising a plurality of slits that are in communication with the internal lumen, the plurality of slits adapted to allow the first osteogenic composition contained in the internal lumen, to be dispersed out of the internal lumen and delivered to a first bone structure when the elongated threaded member is engaged thereto.

In some embodiments of the invention, the first direction of the first thread is the same as the second direction of the second thread.

In some embodiments, the first direction of the first thread is opposite the direction of the second thread, i.e., reverse threads, whereby, when the first and second threaded ends of the elongated threaded member are disposed proximate separate bone structures, such as an ilium and sacrum, or inserted into pilot openings therein, and the elongated threaded member is rotated in a first direction, the first and second threaded ends advance into the bone structures and provide a compressive or coupling force therebetween.

In some embodiments of the invention, the first and second threads comprise a pitch defining coarse threads.

In some embodiments of the invention, the first and second threads comprise a pitch defining fine threads.

In some embodiments of the invention, the first thread comprises a pitch defining a coarse thread, and the second thread comprises a pitch defining a fine thread.

In some embodiments of the invention, the first thread comprises a pitch defining a fine thread, and the second thread comprises a pitch defining a coarse thread.

In some embodiments of the invention, the first threaded end and/or second threaded end of the elongated threaded member comprises a plurality of apertures that are also in communication with the internal lumen of the elongated threaded member, the first plurality of apertures similarly adapted to allow the osteogenic composition to be dispersed out of the internal lumen and delivered to the first bone structure when the elongated threaded member is engaged thereto.

In some embodiments, the osteogenic composition comprises a bone morphogenic protein (BMP) comprising BMP-1, BMP2a, BMP2b, BMP3, BMP4, BMP5, BMP6, BMP7, or BMP8a.

In some embodiments, the osteogenic composition comprises a biologically active agent.

In some embodiments, the biologically active agent comprises a cell, such as, without limitation, a human embryonic stem cell, mesenchymal stem cell, hematopoietic stem cell, bone marrow-derived progenitor cell, bone marrow stromal cell (BMSCs), osteoprogenitor cell, osteoblast, osteocyte, and osteoclast.

In some embodiments, the biologically active agent comprises a growth factor, such as, without limitation, a transforming growth factor-alpha (TGF-$\alpha$), transforming growth factor-beta (TGF-$\beta$), fibroblast growth factor-2 (FGF-2), and vascular endothelial growth factor (VEGF).

In some embodiments, the elongated threaded member comprises a surgical grade metal, such as, without limitation, stainless-steel, titanium, a titanium alloy, a cobalt-chromium alloy, a nickel-titanium alloy, tantalum, and a magnesium ceramic.

In some embodiments, the elongated threaded member comprises a biodegradable material, such as, without limitation, magnesium, a magnesium-aluminum (Mg—Al) alloy, magnesium-rare earth alloy, magnesium-zinc (Mg—Zn) alloy, magnesium-calcium (Mg—Ca) alloy, and zinc-based alloy.

In some embodiments, the elongated threaded member comprises polymeric outer coating, such as, without limitation, a poly(glycerol sebacate) (PGS)—based coating.

In a preferred embodiment, the proximal or end of said elongated threaded member comprises an internal insertion tool engagement region that is sized and configured to receive and cooperate with an external deployment and/or extraction tool or assembly.

In some embodiments of the invention, there are thus also provided methods for stabilizing dysfunctional bone structures.

In one embodiment, the method for stabilizing a dysfunctional bone structure of a subject comprises the steps of:

providing a bone structure prosthesis, the bone structure prosthesis comprising an elongated threaded member adapted to threadably engage the dysfunctional bone structure, the elongated threaded member comprising a first threaded end, a second threaded end that is disposed opposite the first threaded end, and an intervening non-threaded central region that is disposed between the first threaded end and the second threaded end, the elongated threaded member further comprising a proximal end and a distal end disposed opposite the proximal end, the distal end comprising a closed configuration, the first threaded end comprising a first thread that extends from the non-threaded central region to the distal end of the first threaded end, the first thread disposed and positioned on the first threaded end in a substantially helical manner in a first direction, the second threaded end comprising a second thread that extends from the non-threaded central region to the proximal end of the second threaded end, the second thread disposed and positioned on the second threaded end in a substantially helical manner in a second direction, the elongated threaded member further comprising an internal lumen that extends longitudinally through the elongated threaded member, the elongated threaded member further comprising an osteogenic composition, the osteogenic composition disposed in the internal lumen, the non-threaded central region of the elongated threaded member comprising a plurality of slits that are in communication with the internal lumen, the plurality of slits adapted to allow the first osteogenic composition contained in the internal lumen, to be dispersed out of the internal lumen and delivered to a first bone structure when the elongated threaded member is engaged thereto;

creating a pilot opening in the dysfunctional bone structure; and inserting the prosthesis into the pilot opening of the dysfunctional bone structure.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 5G is a right-side plan view of the prosthesis shown in FIG. 5A, in accordance with the invention;

FIG. 5H is a right-side sectional plan view of the prosthesis shown in FIG. 5A, in accordance with the invention;

FIGS. 8C through 8J are perspective views of further embodiments of elongated threaded prostheses comprising dual threaded ends, in accordance with the invention;

FIG. 10A is a perspective view of another embodiment of an elongated threaded prosthesis, i.e., bone structure screw, in accordance with the invention;

FIG. 10B is an end plan view of the elongated threaded prosthesis shown in FIG. 10A, in accordance with the invention;

FIG. 10C is a perspective view of another embodiment of the elongated threaded prosthesis shown in FIG. 10A, in accordance with the invention;

FIG. 11A is a perspective view of one embodiment of an elongated non-threaded prosthesis, in accordance with the invention;

FIG. 11B is a perspective view of another embodiment of an elongated non-threaded prosthesis, in accordance with the invention;

FIG. 11C is a perspective view of yet another embodiment of an elongated non-threaded prosthesis, in accordance with the invention;

FIGS. 11D through 11H are end plan views of elongated non-threaded prostheses, showing various cross-sectional shapes, in accordance with the invention;

FIG. 12A is a perspective view of another embodiment of an elongated non-threaded prosthesis, in accordance with the invention;

FIG. 12B is a right-side plan view of the elongated non-threaded prosthesis shown in FIG. 12A, in accordance with the invention;

FIG. 12C is an end plan view of the elongated non-threaded prosthesis shown in FIG. 12A, in accordance with the invention;

FIG. 13A is a perspective view of another embodiment of an elongated non-threaded prosthesis, in accordance with the invention; and FIG. 13B is a right-side plan view of the elongated non-threaded prosthesis shown in FIG. 13A, in accordance with the invention.

DETAILED DESCRIPTION OF THE PREFERRED EMBODIMENT

Figure 1:
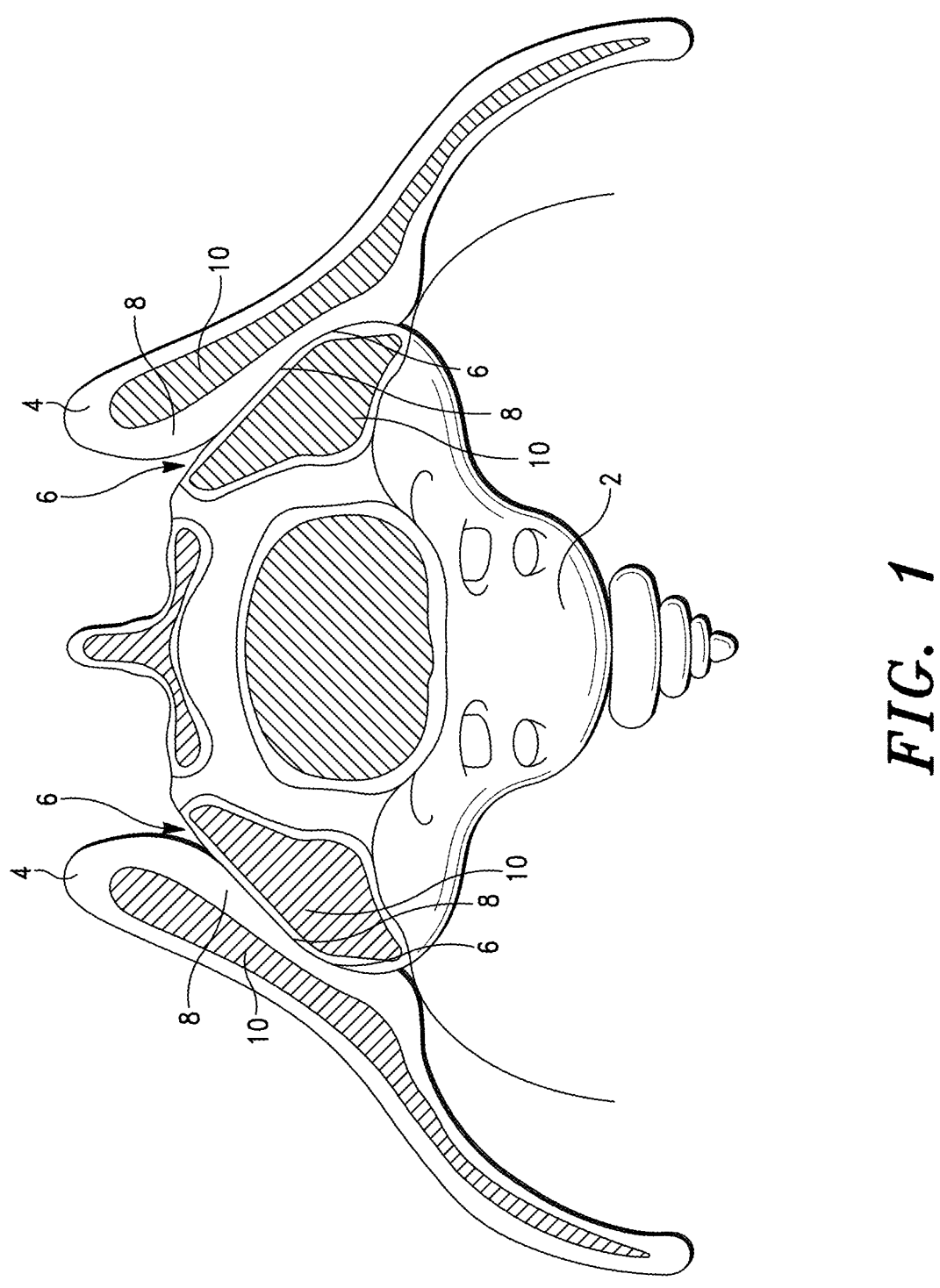
FIG. 1 is a schematic illustration of a human pelvic region from an anteroposterior (AP) perspective showing the SI joints thereof.

Before describing the present invention in detail, it is to be understood that this invention is not limited to particularly exemplified apparatus, systems, structures or methods as such may, of course, vary. Thus, although a number of apparatus, systems, structures and methods similar or equivalent to those described herein can be used in the practice of the present invention, the preferred apparatus, systems, structures and methods are described herein.

It is also to be understood that, although the present invention is primarily described and illustrated in connection with bone structure prostheses and methods for stabilizing dysfunctional sacroiliac (SI) joints, the invention is not limited to such prostheses and methods. According to the invention, the apparatus, systems, structures and methods of the invention can also be employed to stabilize other articulating bone structures, and non-articulating bone structures, such as intervertebral joints. The apparatus, systems, structures and methods of the invention can also be employed to stabilize individual skeletal members, i.e., bones, including, without limitation, spinal vertebrae, intertarsal bones, femurs, and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "bone" and "bone structure" are used interchangeably herein, and mean and include any skeletal member or structure that comprises osseous tissue. The terms "bone" and "bone structure" thus mean and include complete and partial skeletal members or bone structures, including articulating and non-articulating bone structures, (e.g., vertebrae, sacrum, ilium, femur, etc.) and portions thereof.

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The terms "joint" and "junction" are used interchangeably herein, and mean and include any region proximate to non-articulating and articulating regions of bone structures and, hence, a junction between and defined by the bone structures. The terms "joint" and "junction" thus mean and include, without limitation, SI joints, intervertebral joints, facet joints, intertarsal joints including, subtalar joints, talo-calcaneonavicular joints, calcaneocuboid joints; and like joint structures.

The term "dysfunctional" as used in connection with a bone structure, means and includes a physiological abnormality, disorder or impairment of a bone structure, including, but limited to, traumatic fracture and/or dislocation of a bone structure, e.g., SI joint, vertebrae, sacrum, ilium, femur, etc., degenerative arthritis, and/or an inflammation or degenerative condition of a bone structure.

The terms "articular surface" and "articulating surface" are used interchangeably herein in connection with bone structures, and mean and include a surface of a bone structure that forms an articulating junction with an adjacent bone structure, e.g., the articular surfaces of the sacrum and ilium bone structures.

The terms "fusion", "arthrodesis", and "fixation" are used interchangeably herein in connection with bone structures, and mean and include partial or complete immobilization of bone structures.

The term "stabilization", as used herein, means and includes reinforcing, e.g., supporting, or modulating motion of bone structures. The term "stabilization", thus, in some instances, means and includes fusion, arthrodesis and fixation of adjacent bone structures, such as articular bone structures, and portions of a fractured bone structure, e.g., fractured femur.

The term "prosthesis", as used herein in connection with bone structures, means and includes a system or apparatus configured and adapted to stabilize or modulate motion of bone structures.

The term "biodegradable", as used herein, means the ability of a material; particularly, a polymer or adhesive, to breakdown and be absorbed within the physiological environment of a joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly(lactic-co-glycolic) acid (PLGA) and poly($\varepsilon$-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly(polyol sebacate) (PPS), poly(xylitol sebacate) (PXS), poly(xylitol glutamate sebacate) (PXGS), hydroxybutyrate-hydroxyvalerate copolymers, polyesters such as, but not limited to, aspartic acid and different aliphatic diols; poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly($\gamma$-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); poly(ethylene glycol) (PEG) based compositions, including FocalSeal®, Progel™ Duraseal™, DuraSeal™ Xact, Coseal®, and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue. The term "osteogenic composition", thus, in some instances means and includes an agent or composition that promotes, induces or modulates fusion, arthrodesis, and/or fixation of bone structures.

The term "osteogenic composition" thus also means and includes, without limitation, the following osteogenic materials and compositions comprising same: demineralized bone matrix, autograft bone material, allograft bone material, xenograft bone material, polymethyl-methacrylate, calcium-based bone void filler material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly(ethylene glycol) (PGS-PEG); and/or composites thereof, e.g., PGS-hydroxyapatite (HA) composites and PGS-poly($\varepsilon$-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., promotes and/or induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage, and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)), and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2), and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs), and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition, or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab, disease-modifying anti-rheumatic drugs (DMARDs), including methotrexate and hydroxychloroquine, antibiotics, anti-viral agents, steroidal anti-inflammatories, non-steroidal anti-inflammatories, anti-thrombotic agents, including anti-coagulants and anti-platelet agents; and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®), and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin, and rifampin.

The terms "anti-inflammatory" and "anti-inflammatory agent" are also used interchangeably herein, and mean and include a "pharmacological agent", which, when a therapeutically effective amount is administered to a subject, prevents, or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac, and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles, and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to apparatus, i.e., bone structure prostheses, and methods for stabilizing dysfunctional bone structures.

Figure 3A:
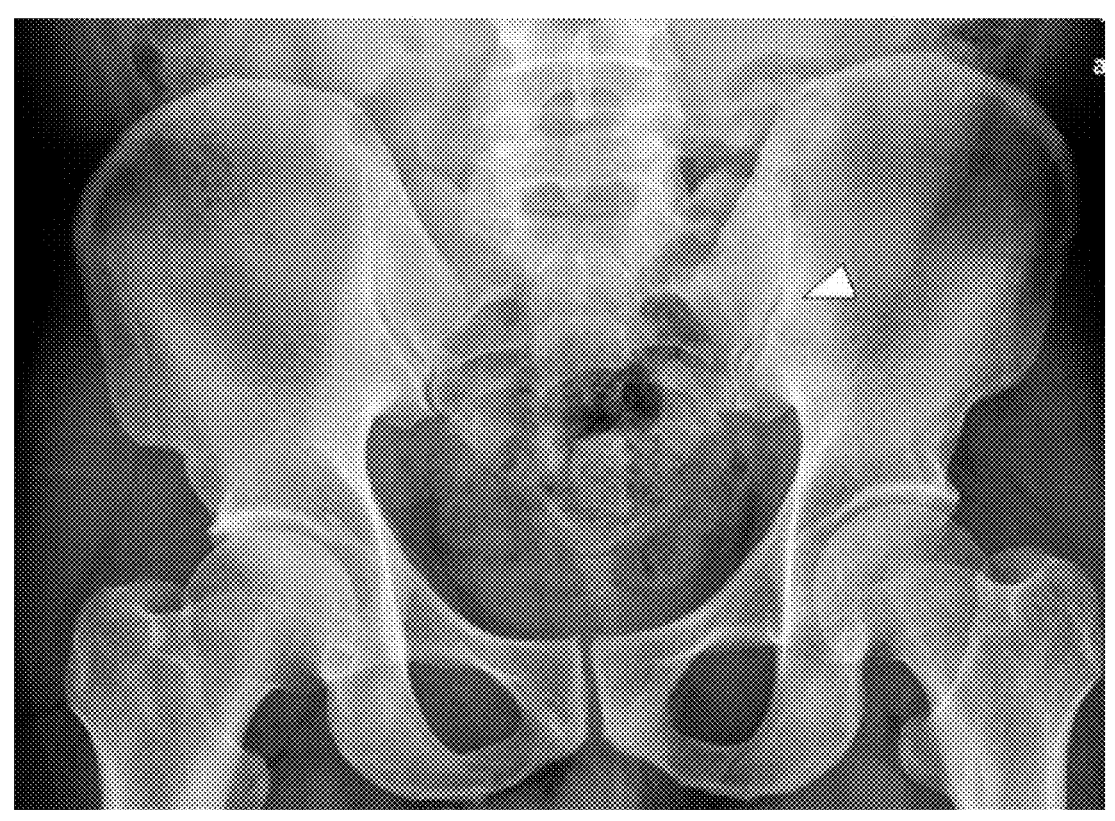
FIG. 3A is a magnetic resonance image (MRI) of a dysfunctional SI joint from an AP perspective.
Figure 3B:
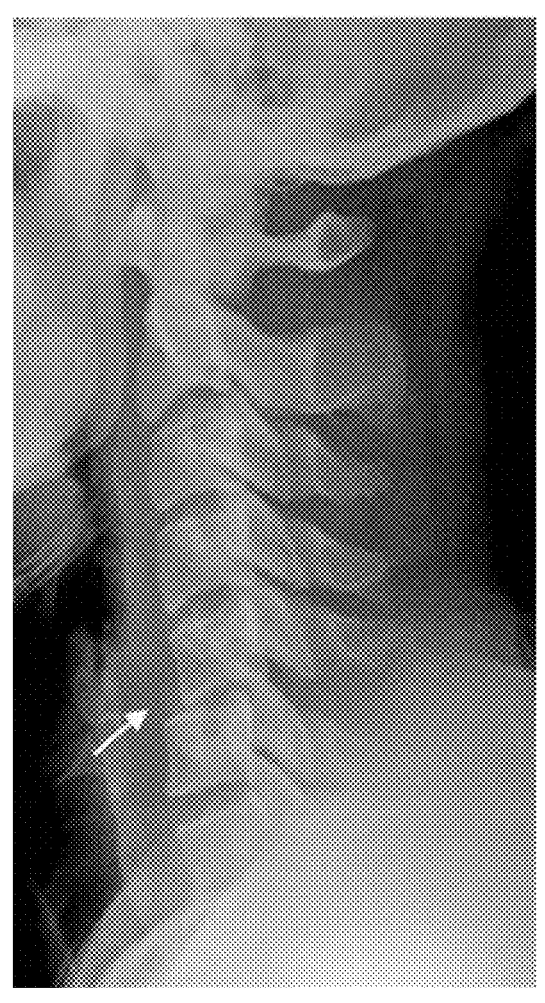
FIG. 3B is an MRI of a dysfunctional intervertebral joint from a lateral perspective.
Figure 3C:
FIG. 3C is an MRI of a fractured femur from an AP perspective.

As indicated above, although the present invention is primarily described and illustrated in connection with bone structure prostheses and methods for stabilizing dysfunctional sacroiliac (SI) joints, such as the dysfunctional SI joint shown in FIG. 3A, the invention is not limited to such prostheses and methods. Indeed, according to the invention, the bone structure prostheses and methods of the invention can also be readily employed to stabilize other dysfunctional bone structures, including other dysfunctional articulating bone structures, such as the dysfunctional intervertebral joint shown in FIG. 3B, dysfunctional non-articulating bone structures, such as a dysfunctional pelvic girdle, and dysfunctional individual skeletal members, such as the fractured femur shown in FIG. 3C.

In some embodiments of the invention, there are thus provided bone structure prostheses and methods for stabilizing dysfunctional articulating bone structures. In a preferred embodiment, the noted prostheses and systems can be readily employed in a minimally-invasive manner.

In some embodiments of the invention, there are also provided bone structure prostheses and methods for stabilizing dysfunctional non-articulating bone structures and dysfunctional individual skeletal members.

According to the invention, the bone structure prostheses of the invention can comprise various configurations, including pontoon shaped members, elongated threaded members, such as screws, and elongated non-threaded members, such as pins and wedges.

As indicated above, articulating bone structure, i.e., joint, stabilization methods typically comprise surgical placement of a prosthesis proximate to or in a dysfunctional bone structure via anterior, lateral, and posterior approaches to the joint.

Referring back to FIG. 1, an anterior approach to an articulating bone structure, which in this instance is a SI joint 6 (and, hence, a dysfunctional SI joint), would be substantially perpendicular to the page upon which FIG. 1 is printed.

Figure 2:
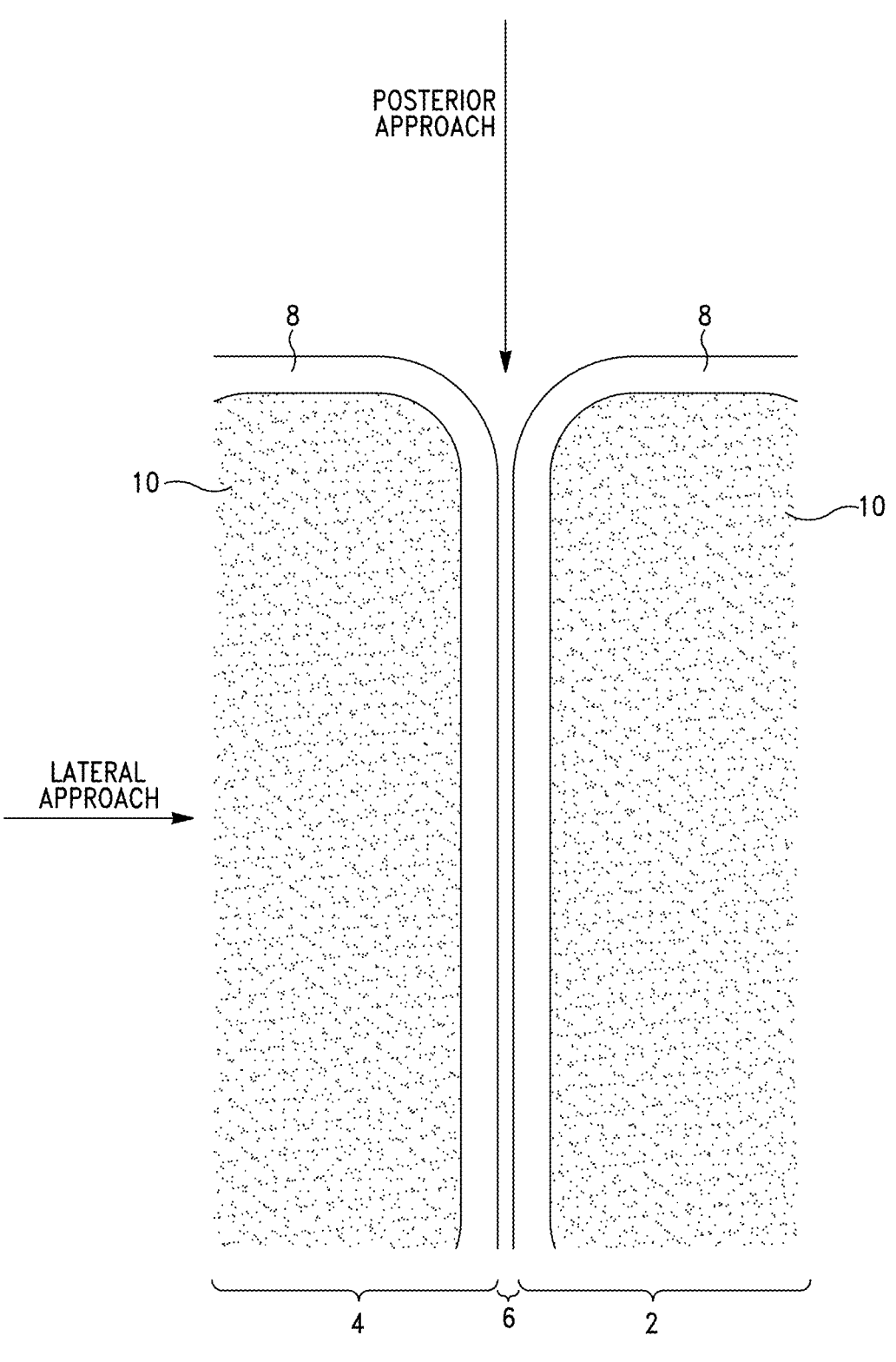
FIG. 2 is an illustration of a SI joint showing lateral and posterior approaches to the SI joint, in accordance with the invention.

Referring now to FIG. 2 there is shown a close-up illustration of a portion of the leftmost SI joint 6 illustrated in FIG. 1, showing approximate approach vectors for lateral and posterior approaches to the SI joint 6.

As indicated above, in some embodiments of the invention, there are provided bone structure prostheses and methods for stabilizing dysfunctional articulating bone structures. In a preferred embodiment of the invention, the prostheses are configured and adapted to be implanted in dysfunctional articulating bone structures in a minimally invasive manner.

In some embodiments, such as stabilizing a dysfunctional SI joint, the bone structure prostheses of the invention are configured and adapted to be implanted in dysfunctional articulating bone structures via a posterior approach.

According to the invention, suitable bone structure prostheses for stabilizing dysfunctional articulating bone structures; particularly, dysfunctional SI joints, are set forth in Co-pending application Ser. No. 17/463,831, which is expressly incorporated by reference herein in its entirety.

As also set forth in Co-pending U.S. application Ser. No. 17/463,831, the bone structure prostheses are configured and adapted to be implanted in pilot openings in the dysfunctional articulating bone structures to stabilize the dysfunctional structures.

Referring now to FIGS. 5A-5I, one embodiment of a bone structure prosthesis that is specifically designed and configured to stabilize a dysfunctional SI joint will be described in detail. Although the prosthesis (denoted "70") is described in connection with stabilizing a dysfunctional SI joint, according to the invention, the prosthesis can also be employed to stabilize other articulating and non-articulating bone structures, including individual skeletal members.

As set forth in Co-pending U.S. application Ser. No. 17/463,831, prosthesis 70 is particularly adapted, configured, and suitable for stabilizing dysfunctional SI joints via a posterior approach.

As also set forth in Co-pending U.S. application Ser. No. 17/463,831 and discussed in detail below, the "pontoon shaped" prosthesis 70 is configured and adapted to be inserted into pilot openings in dysfunctional bone structures; particularly, dysfunctional SI joints, such as pilot SI joint openings 100, 200 shown in FIGS. 4A-4C and described below, and into and through articular cartilage and cortical bone (and trabecular bone), which define the joint.

Figure 5A:
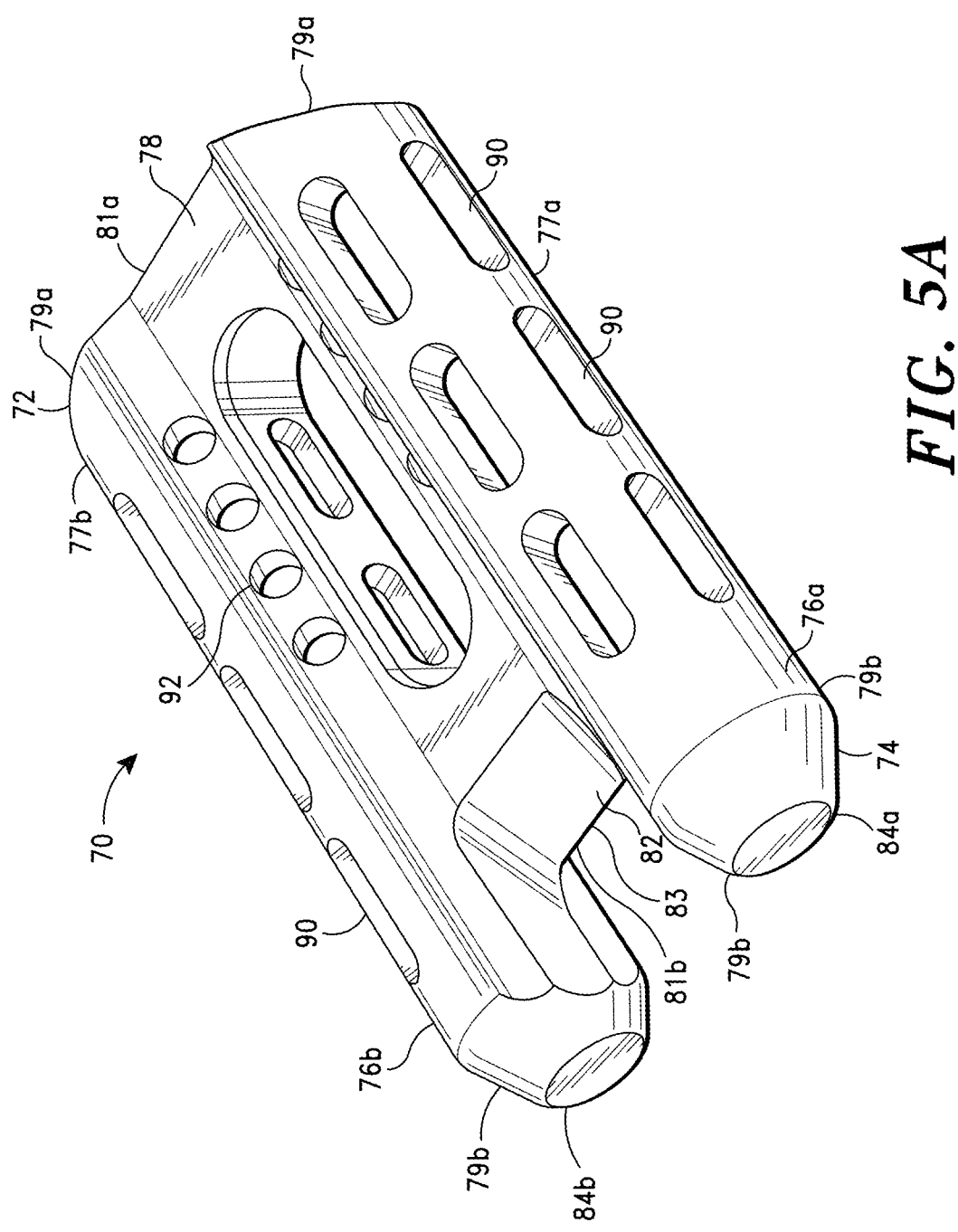
FIG. 5A is a perspective view of one embodiment of a prosthesis, in accordance with the invention.
Figure 5B:
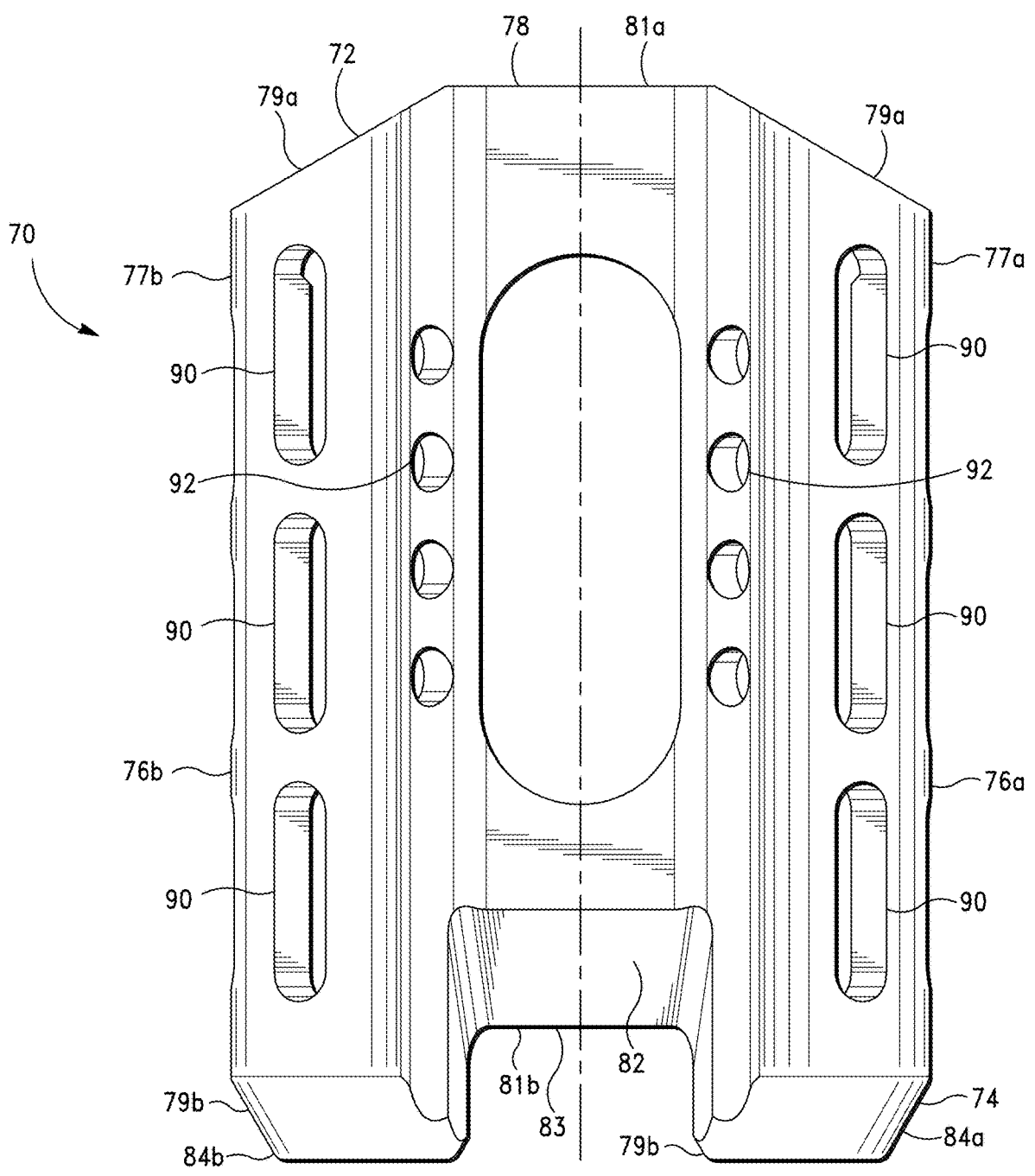
FIG. 5B is a top plan view of the prosthesis shown in FIG. 5A, in accordance with the invention.
Figure 5C:
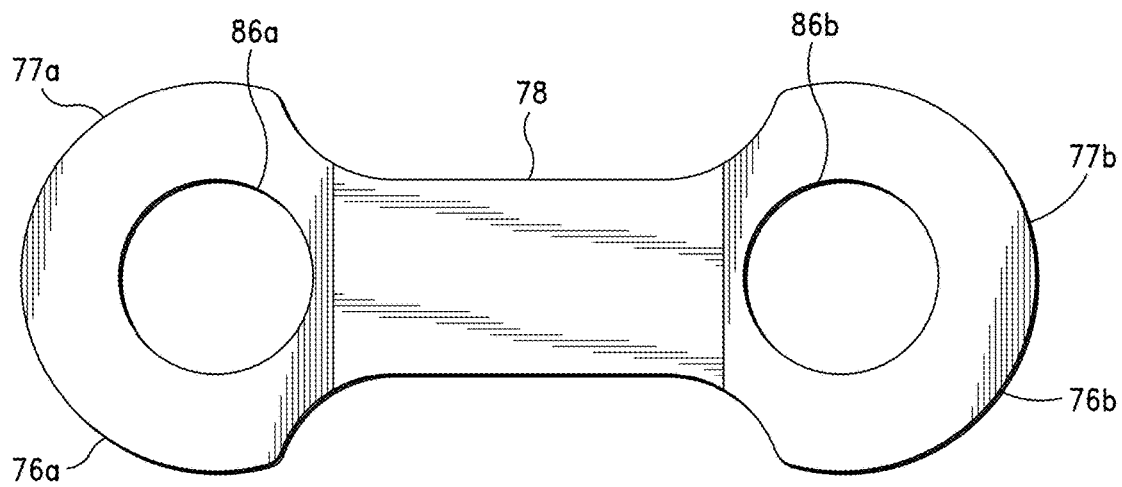
FIG. 5C is a rear plan view of the prosthesis shown in FIG. 5A, in accordance with the invention.
Figure 5D:
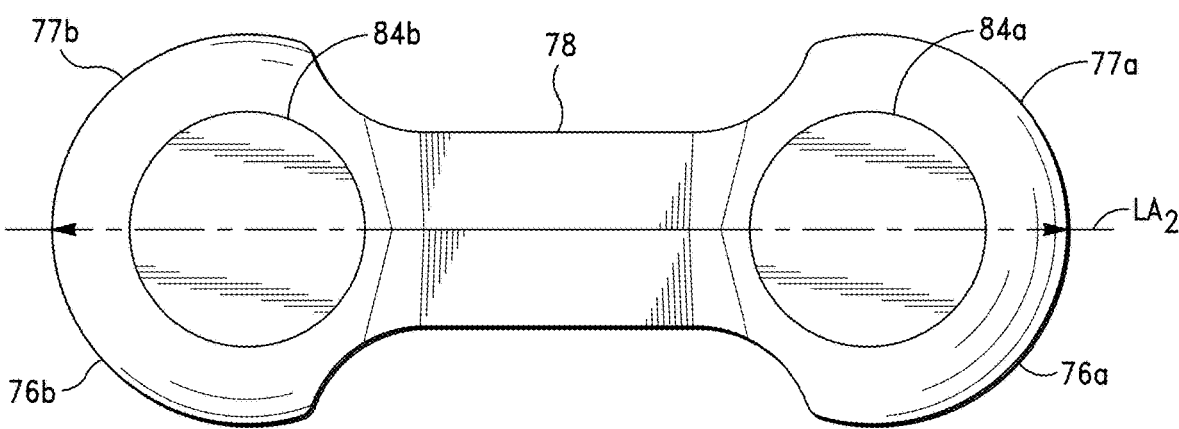
FIG. 5D is a front plan view of the prosthesis shown in FIG. 5A, in accordance with the invention.
Figures 5E, 5F:
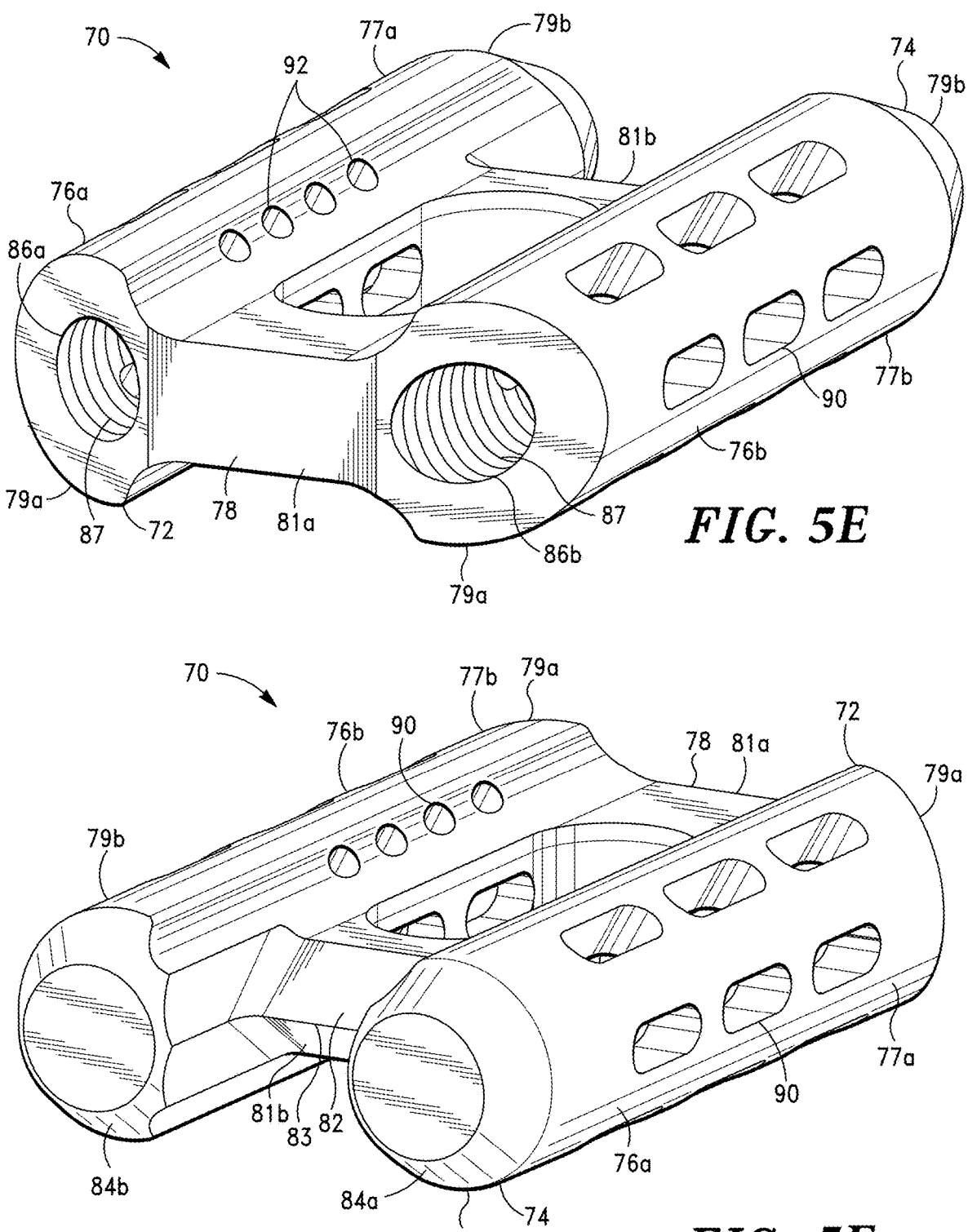
FIG. 5E is a rear perspective view of the prosthesis shown in FIG. 5A, in accordance with the invention.
FIG. 5F is a front perspective view of the prosthesis shown in FIG. 5A, in accordance with the invention.

As illustrated in FIGS. 5A, 5E, and 5F, the prosthesis 70 comprises a biocompatible and, hence, implantable member comprising proximal and distal ends 72, 74, and first and second elongated partially cylindrical sections 76a, 76b connected to a bridge section 78, whereby the prosthesis 70 comprises a continuous exterior surface comprising first and second partially cylindrical surface regions 77a, 77b.

As further illustrated in FIGS. 5A, 5E, and 5F, the first and second partially cylindrical sections 76a, 76b comprise proximal and distal ends 79a, 79b. The bridge section 78 similarly comprises proximal and distal ends 81a, 81b.

As set forth in Co-pending U.S. application Ser. No. 17/463,831, the prosthesis 70 can comprise any suitable length from the proximal ends 79a to the distal ends 79b of the partially cylindrical sections 76a, 76b. In some embodiments, the prosthesis 70 comprises a length in the range of 20-50 mm, more preferably, a length in the range of 30-40 mm.

Figure 4A:
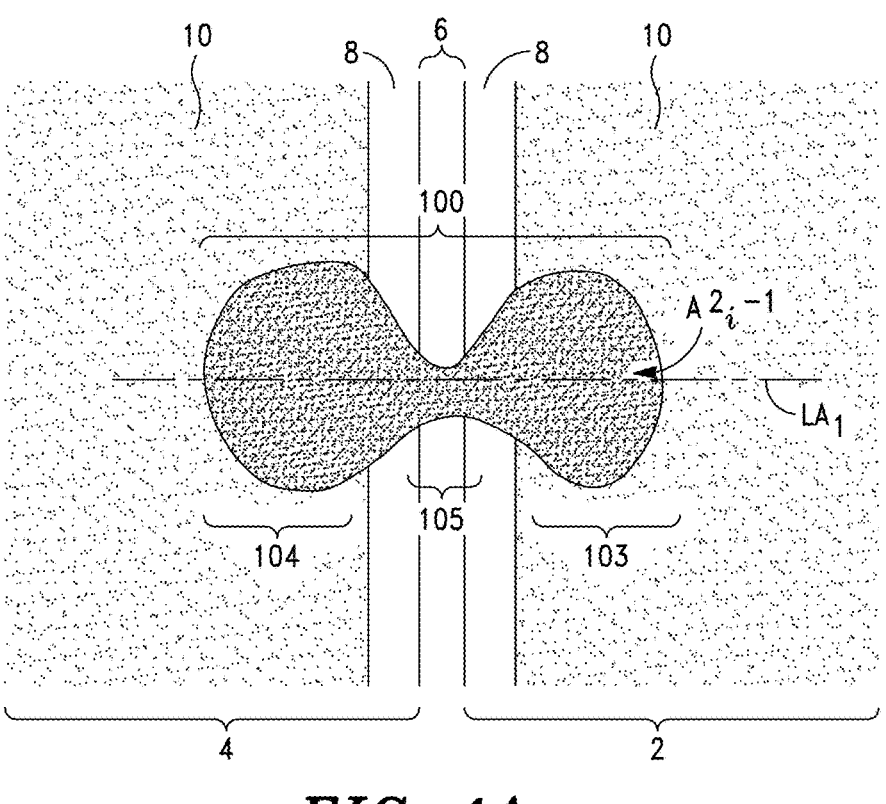
FIG. 4A is an illustration of a SI joint shown showing one embodiment of a pilot SI joint opening, in accordance with the invention.
Figure 4B:
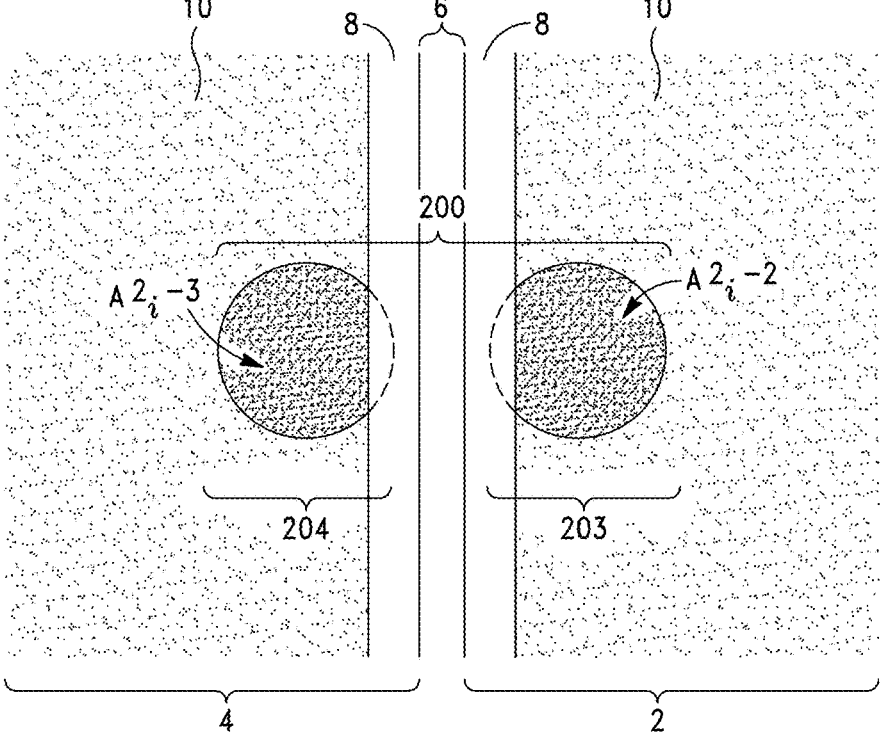
FIGS. 4B and 4C are illustrations of further embodiments of SI joint openings, in accordance with the invention.

As illustrated in FIGS. 5C, 5E, and 5F, and FIGS. 4A and 4B, the first partially cylindrical surface region 77a preferably comprises a partially cylindrical surface region shape that corresponds to at least a portion of the first lobe region 103 of the pilot SI joint opening 100 shown in FIG. 4A and/or the sacrum guide portion 203 of the pilot SI joint opening 200 shown in FIG. 4B, and/or the second lobe region 104 of the pilot SI joint opening 100 and/or the ilium guide portion 204 of the pilot SI joint opening 200, depending on the entry position of the prosthesis 70 into the pilot SI joint openings 100, 200.

The second partially cylindrical surface region 77b similarly preferably comprises a partially cylindrical surface region shape that corresponds to at least a portion of the first lobe region 103 of the pilot SI joint opening 100 shown in FIG. 4A and/or the sacrum guide portion 203 of the pilot SI joint opening 200 shown in FIG. 4B, or the second lobe region 104 of the pilot SI joint opening 100 and/or the ilium guide portion 204 of the pilot SI joint opening 200, again depending on the entry position of the prosthesis 70 into the pilot SI joint openings 100, 200.

As illustrated in FIGS. 5A, 5B, and 5F-5H, the distal end 81b of the bridge section 78 preferably comprises a taper region 82, which is configured and adapted to disrupt, i.e., cut into and through, articular cartilage and cortical bone 8 (and, in some aspects, trabecular bone 10), which define a SI joint.

As also set forth in Co-pending U.S. application Ser. No. 17/463,831, the taper region 82 of the bridge section 78 can comprise various configurations including, without limitation, X-bevel, wedge-shaped or bevel, including top and bottom wedge bevels; Y-bevel, including top and bottom Y-bevels; and K-bevel configurations.

In some embodiments, the taper region 82 comprises two angled regions that intersect at a central point 83, i.e., pointed proximate the mid-region of the bridge section 78, such as shown in FIGS. 5A and 5F. In some embodiments, the taper region 82 comprises a single angled or sloped region defining a plane that intersects the plane defined by the bottom surface of the prosthesis 70, i.e., wedge shaped or bevel configuration.

As further illustrated in FIG. 5A, the distal ends 79b of the first and second elongated partially cylindrical sections 76a, 76b also preferably comprise tapered regions 84a, 84b, which facilitate (i) insertion of the distal ends 79b of the first and second elongated partially cylindrical sections 76a, 76b into the first and second lobe regions 103, 104 of the pilot SI joint opening 100 shown in FIG. 4A and/or the sacrum and ilium guide portions 203, 204 of the pilot SI joint opening 200 shown in FIG. 4B, and (ii) as discussed in detail in Co-pending U.S. application Ser. No. 17/463,831, in some embodiments, transition of the pilot SI joint opening 100 from a first configuration and size (and, hence, cross-sectional area, i.e., $A^2_i$-1 shown in FIG. 4A) to a second expanded configuration and size (and, hence, cross-sectional area, i.e., $A^2$-4 shown in FIG. 7A) when the prosthesis 70 is inserted therein, and transition of the sacrum and ilium guide portions 203, 204 of pilot SI opening 200 from first configurations and sizes (and, hence, cross-sectional areas, i.e., $A^2_i$-2 and $A^2_i$-3 shown in FIG. 4B) to expanded second configurations and sizes (and, hence, cross-sectional areas, i.e., $A^2$-5 and $A^2$-6 shown in FIG. 7B) when the prosthesis 70 is inserted therein.

As illustrated in FIGS. 5C, 5E, and 5H, the first elongated partially cylindrical section 76a of the prosthesis 70 comprises an internal prosthesis engagement member lumen 86a that extends from the proximal end 79a of the first elongated partially cylindrical section 76a.

As illustrated in FIGS. 5C and 5E, the second elongated partially cylindrical section 76b of the prosthesis 70 also comprises an internal prosthesis engagement member lumen 86b that extends from the proximal end 79a of the first elongated partially cylindrical section 76b.

As set forth in Co-pending U.S. application Ser. No. 17/463,831, in a preferred embodiment, the internal prosthesis engagement member lumens 86a, 86b of the prosthesis 70 are sized and configured to receive a prosthesis deployment assembly that is designed and configured to engage and position the prosthesis 70 in a pilot opening and, thereby, in a dysfunctional SI joint.

Details of the preferred prosthesis deployment assembly, the engagement thereof to prosthesis 70 and positioning of prosthesis 70 in a pilot opening and, thereby, in a dysfunctional SI joint are set forth in Co-pending U.S. application Ser. No. 17/463,831.

In a preferred embodiment, the internal prosthesis engagement lumens 86a, 86b are also configured to receive agents and compositions that further facilitate adhesion of the prosthesis 70 to pilot openings of the invention; particularly, pilot SI openings 100, 200, and, thereby, bone structures. Such agents and compositions are set forth in in Co-pending U.S. application Ser. No. 17/463,831.

In a preferred embodiment, the internal prosthesis engagement lumens 86a, 86b are also configured to receive the aforementioned biologically active agents and compositions, including osteogenic agents and compositions, and pharmacological agents and compositions that promote or induce proliferation, and/or growth and/or remodeling and/or regeneration of osseous tissue and/or facilitate osseous tissue ingrowth into the prosthesis 70 when the prosthesis 70 is disposed in a pilot opening and, hence, engaged to bone structures.

Referring back to FIGS. 5A and 5B, in a preferred embodiment, the prosthesis 70 further comprises a plurality of slots 90 and holes 92, which preferably are in communication with the internal prosthesis engagement member lumens 86a, 86b.

Figure 4C:
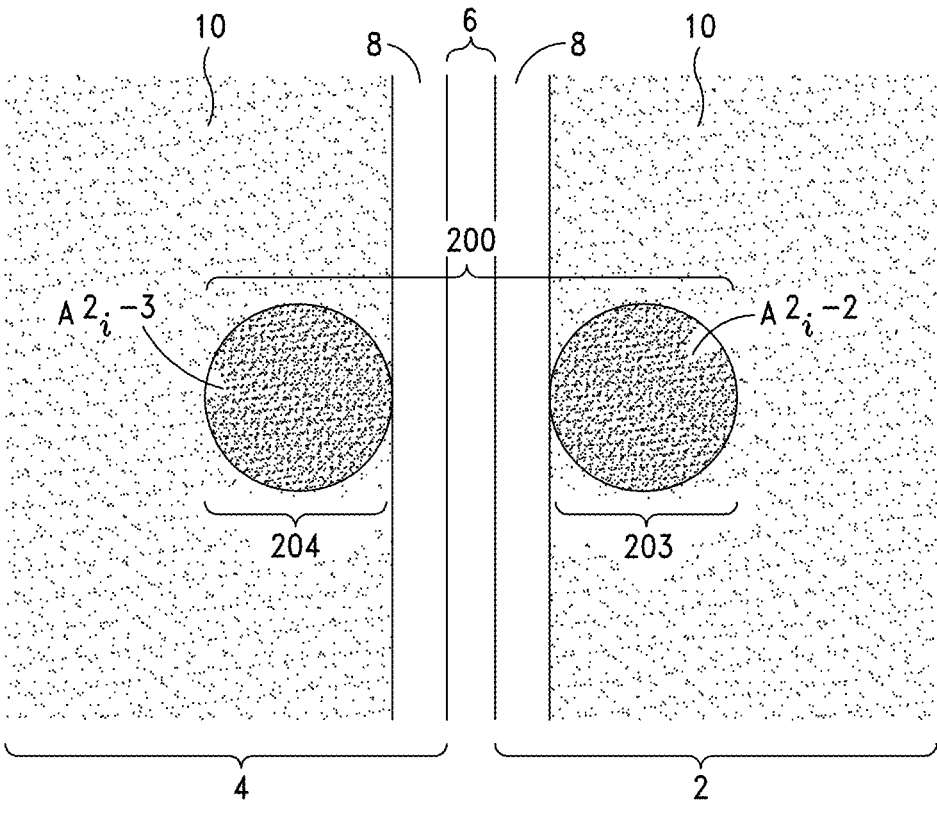

In a preferred embodiment, the agents and compositions referenced above are adapted to extrude through the slots 90 and holes 92 of the prosthesis 70 when the prosthesis 70 is inserted in a pilot opening, such as pilot SI joint openings 100 or 200 shown in FIGS. 4A-4C, to, as indicated above, (i) further promote adhesion of the prosthesis 70 to the pilot openings and, thereby, bone structures (e.g., sacrum and/or ilium), and (ii) promote osseous or bone tissue ingrowth into the prosthesis 70 and healing of the bone structures.

Figure 5I:
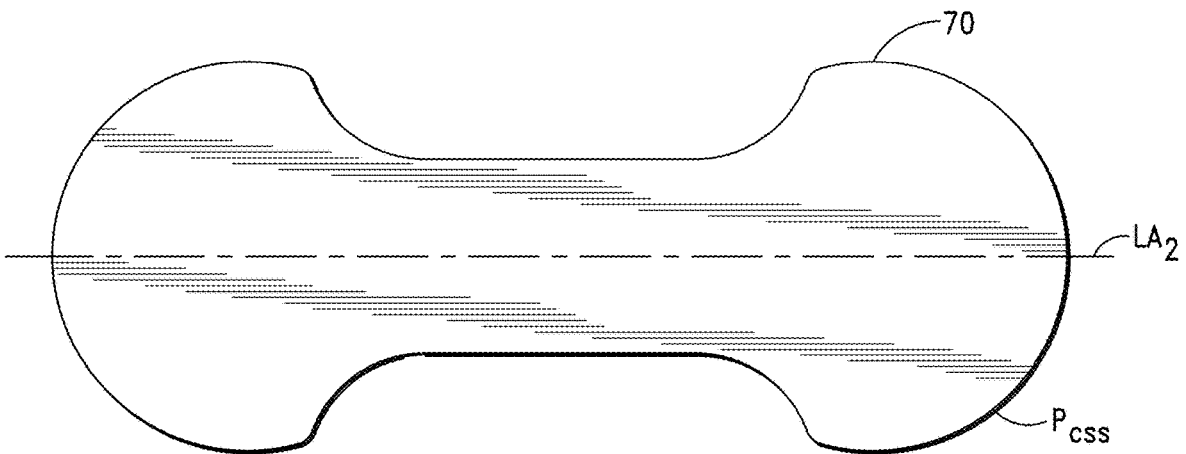
FIG. 5I is another rear plan view of the prosthesis shown in FIG. 5A showing the cross-sectional shape defined by the outer surface of the prosthesis, in accordance with the invention.

Referring now to FIG. 5I, the continuous exterior surface of the prosthesis 70, which is illustrated in FIGS. 5C and 5D, defines a prosthesis cross-sectional shape (denoted "$P_{CSS}$") having a longitudinal axis $LA_2$.

Figure 6A:
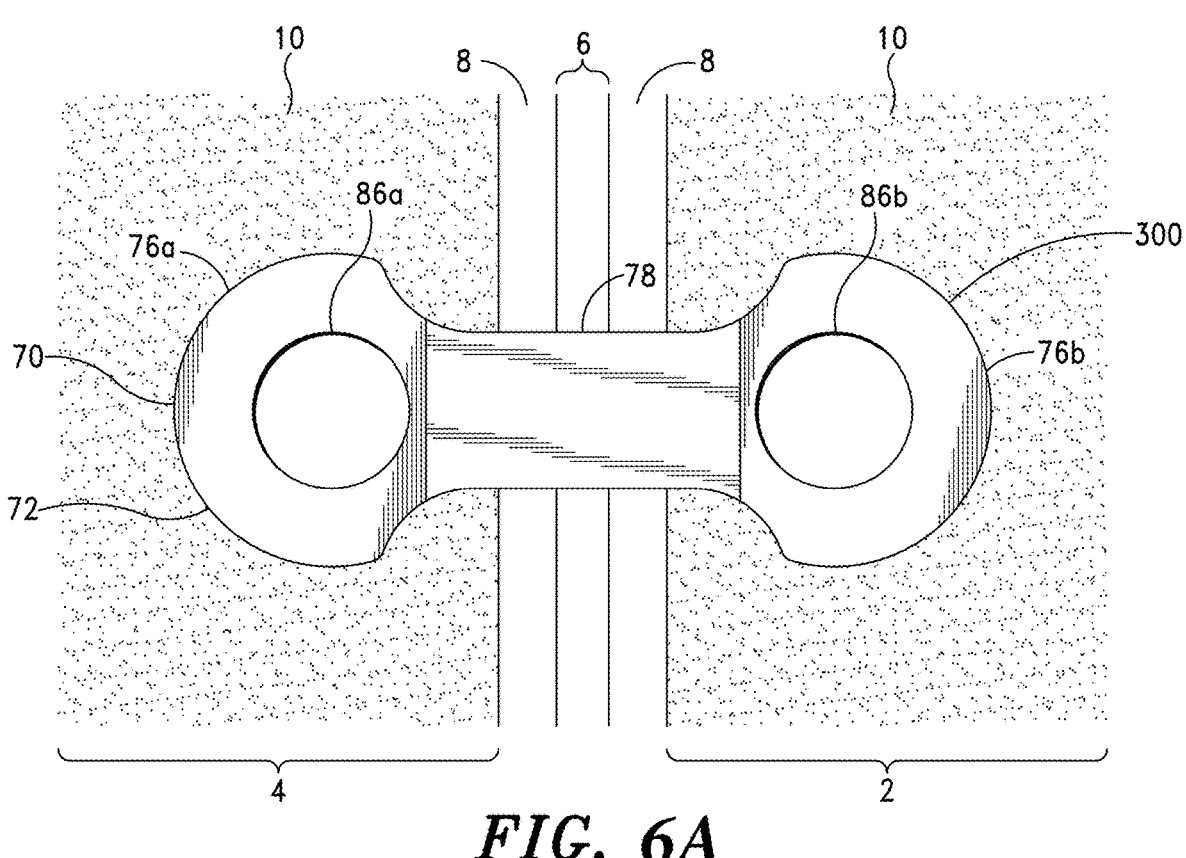
FIG. 6A is an illustration of the prosthesis shown in FIG. 5A inserted into the pilot SI joint opening shown in FIG. 4A and the resulting or induced post-prosthesis insertion SI joint opening, in accordance with the invention.
Figure 6B:
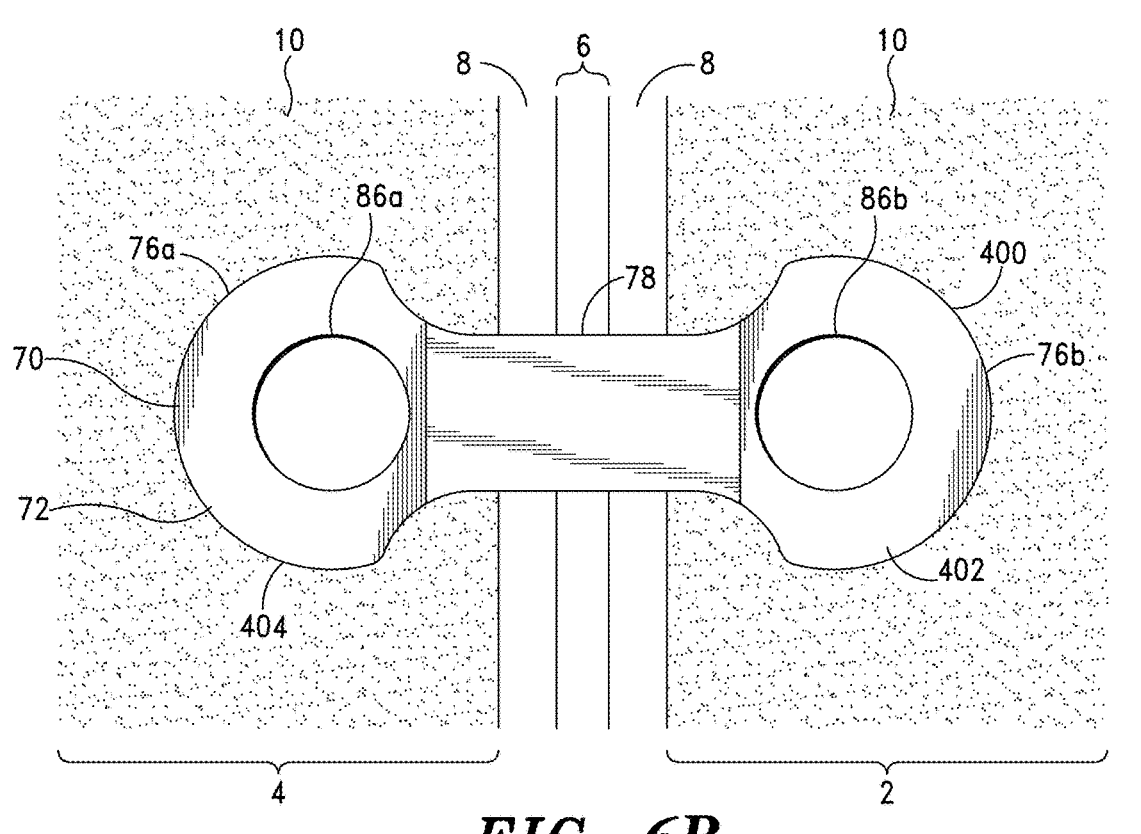
FIG. 6B is an illustration of the prosthesis shown in FIG. 5A inserted in the pilot SI joint opening shown in FIG. 4B and the resulting or induced post-prosthesis insertion SI joint opening, in accordance with the invention.

According to one embodiment of the invention, the length of the prosthesis cross-sectional shape $P_{CSS}$ along longitudinal axis $LA_2$ is greater than the length of the pilot SI joint opening 100, i.e., cross-sectional shape thereof illustrated in FIG. 4A, along the longitudinal axis $LA_1$ thereof, whereby, when the prosthesis 70 is inserted into a pilot opening, in this instance, pilot SI joint opening 100, as illustrated in FIG. 6A, the pilot SI opening 100 transitions to a post-prosthesis insertion SI joint opening 300 comprising a larger cross-sectional length shape that corresponds to the length of the prosthesis cross-sectional shape $P_{CCS}$.

As also set forth in Co-pending U.S. application Ser. No. 17/463,831 and illustrated in FIG. 7A, in a preferred embodiment, when the prosthesis 70 is inserted into pilot SI joint opening 100, the cross-sectional area of the post-prosthesis insertion SI joint opening 300 also comprises a cross-sectional area (denoted "$A^2$-4") that is greater than the cross-sectional area $A^2_i$-1 of the pilot SI joint opening 100.

Figure 7A:
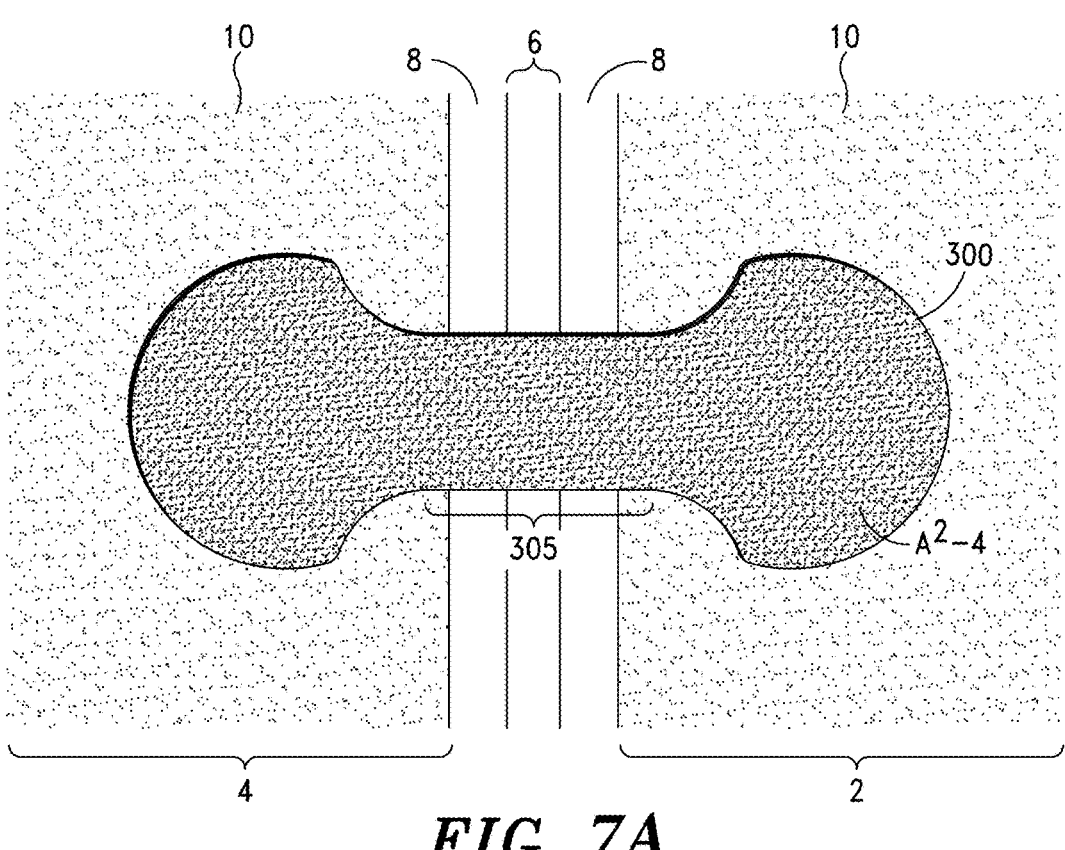
FIG. 7A is an illustration of the post-prosthesis insertion SI joint opening generated or induced when the prosthesis shown in FIG. 5A is inserted in the pilot SI joint opening shown in FIG. 4A, in accordance with the invention.

As further illustrated in FIG. 7A, the noncircular region 105 of pilot SI joint opening 100 also transitions to a much larger noncircular region (denoted "305"), which is achieved by virtue of the tapered bridge section 78 of the prosthesis 70 cutting into and through the articular cartilage and cortical bone 8, which define the SI joint 6, and the trabecular bone 10 proximate the SI joint 6.

As also set forth in Co-pending U.S. application Ser. No. 17/463,831 and illustrated in FIG. 7B, when the prosthesis 70 is inserted into pilot SI joint opening 200, the pilot SI joint opening 200 similarly transitions to a post-prosthesis insertion SI joint opening 400, wherein the cross-sectional areas of the post-prosthesis sacrum and ilium guide portions of the post-prosthesis insertion SI joint opening 400 (now denoted "402" and "404", respectively) comprise greater cross-sectional areas (denoted "$A^2$-5" and "$A^2$-6").

Figure 7B:
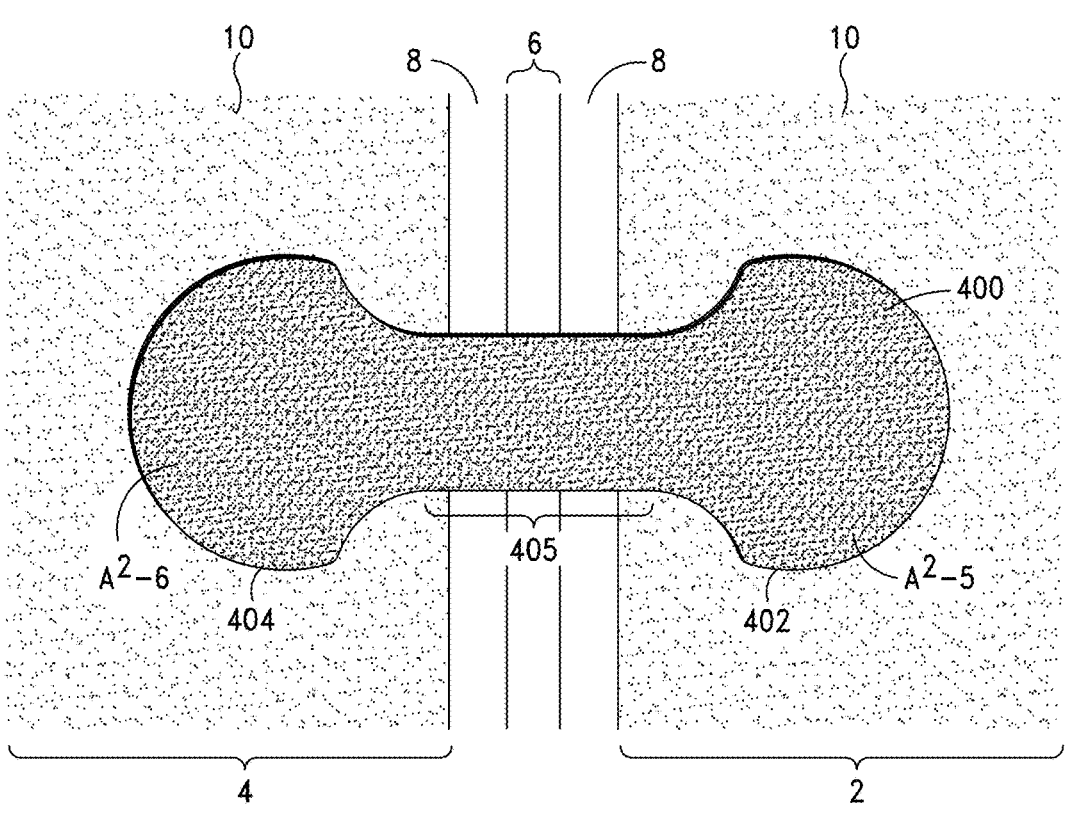
FIG. 7B is an illustration of the post-prosthesis insertion SI joint opening generated or induced when the prosthesis shown in FIG. 5A is inserted in the pilot SI joint opening shown in FIGS. 4B and/or 4C, in accordance with the invention.

As further illustrated in FIG. 7B, the post-prosthesis insertion SI joint opening 400 also comprises a noncircular region (denoted "405"), which is similarly achieved by virtue of the tapered bridge section 78 of the prosthesis 70 cutting into and through the articular cartilage and cortical bone 8, which define the SI joint 6, and the trabecular bone 10 proximate the SI joint 6.

As illustrated in FIGS. 5I, 7A, and 7B, the post-prosthesis insertion SI joint openings 300, 400 also comprise cross-sectional shapes that correspond to the prosthesis cross-sectional shape "$P_{CSS}$" defined by the outer surface of the prosthesis 70, including the first and second elongated partially cylindrical sections 76a, 76b and bridge section 78.

As indicated above, in some embodiments, the prosthesis 70 is specifically configured and adapted to be inserted into pilot SI joint openings 100, 200 shown in FIGS. 4A-4C.

According to the invention, the prosthesis 70 is also configured and adapted to be inserted in similar pilot openings in other articulating and non-articulating bone structures.

As illustrated in FIG. 4A, the pilot SI joint opening 100 comprises a three-dimensional opening comprising first and second lobe regions 103, 104; the first lobe region 103 being disposed in the sacrum 2 and comprising a sacrum opening three-dimensional shape, and the second lobe region 104 being disposed in the ilium 4 and comprising an ilium opening three-dimensional shape.

As also illustrated in FIG. 4A, the three-dimensional pilot SI joint opening 100 is defined in part by at least one noncircular cross-sectional shaped region (denoted "105").

As indicated above, the three-dimensional pilot SI joint opening 100, i.e., cross-sectional shape thereof, also defines a cross-sectional area of the three-dimensional pilot SI joint opening cross-sectional shape (denoted "$A^2_i$-1").

The three-dimensional pilot SI joint opening 100, i.e., cross-sectional shape thereof, also comprises a longitudinal axis (denoted "$LA_1$") in the plane that intersects the sacrum 2 and ilium 4 and an initial pilot SI joint opening length along the axis $LA_1$.

As illustrated in FIG. 4B, the pilot SI joint opening 200 comprises two three-dimensional pilot or guide portions or regions 203, 204; the first guide portion 203 being disposed in the sacrum 2 and the second guide portion 204 being disposed in the ilium 4.

As set forth in Co-pending U.S. application Ser. No. 17/463,831, the sacrum and ilium guide portions 203, 204 can comprise various configurations, e.g., cross-sectional shapes, and sizes to, as indicated above, accommodate insertion of defined regions of prosthesis 70 therein and transition of the sacrum and ilium guide portions 203, 204 from pilot or first configurations and sizes to expanded second configurations and sizes when the prosthesis is inserted therein.

The sacrum and ilium guide portions 203, 204 can also be disposed at various locations in the sacrum 2 and ilium 4, such as shown in FIGS. 4A and 4B.

As further indicated above and illustrated in FIG. 4B, the sacrum and ilium guide portions 203, 204 of the pilot SI joint opening 200, i.e., cross-sectional shape thereof, define cross-sectional areas of the sacrum and ilium guide portions 203, 204 (denoted "$A^2_i$-2" and "$A^2_i$-3", respectively).

The sacrum and ilium guide portions 203, 204 of the pilot SI joint opening 200 are also preferably disposed on a plane that similarly intersects the sacrum 2 and ilium 4.

According to the invention, various apparatus and systems can be employed to create a pilot opening in a dysfunctional articulating bone structure, such as pilot SI openings 100 and 200 shown in FIGS. 4A and 4B. In a preferred embodiment, the pilot openings; particularly, pilot SI openings 100 and 200 are created with a defect creation assembly that is also disclosed in Co-pending U.S. application Ser. No. 17/463,831.

Referring now to FIGS. 8A-8I, 9A-9C, and 10A-10C various embodiments of bone structure prostheses of the invention comprising elongated threaded members will be described in detail.

As indicated above, in some embodiments, such as stabilizing a dysfunctional SI joint, the bone structure prostheses discussed below are configured and adapted to stabilize dysfunctional bone structures via a posterior approach.

In some embodiments, the bone structure prostheses are configured and adapted to stabilize dysfunctional bone structures via a lateral approach.

Figures 8A, 8B:
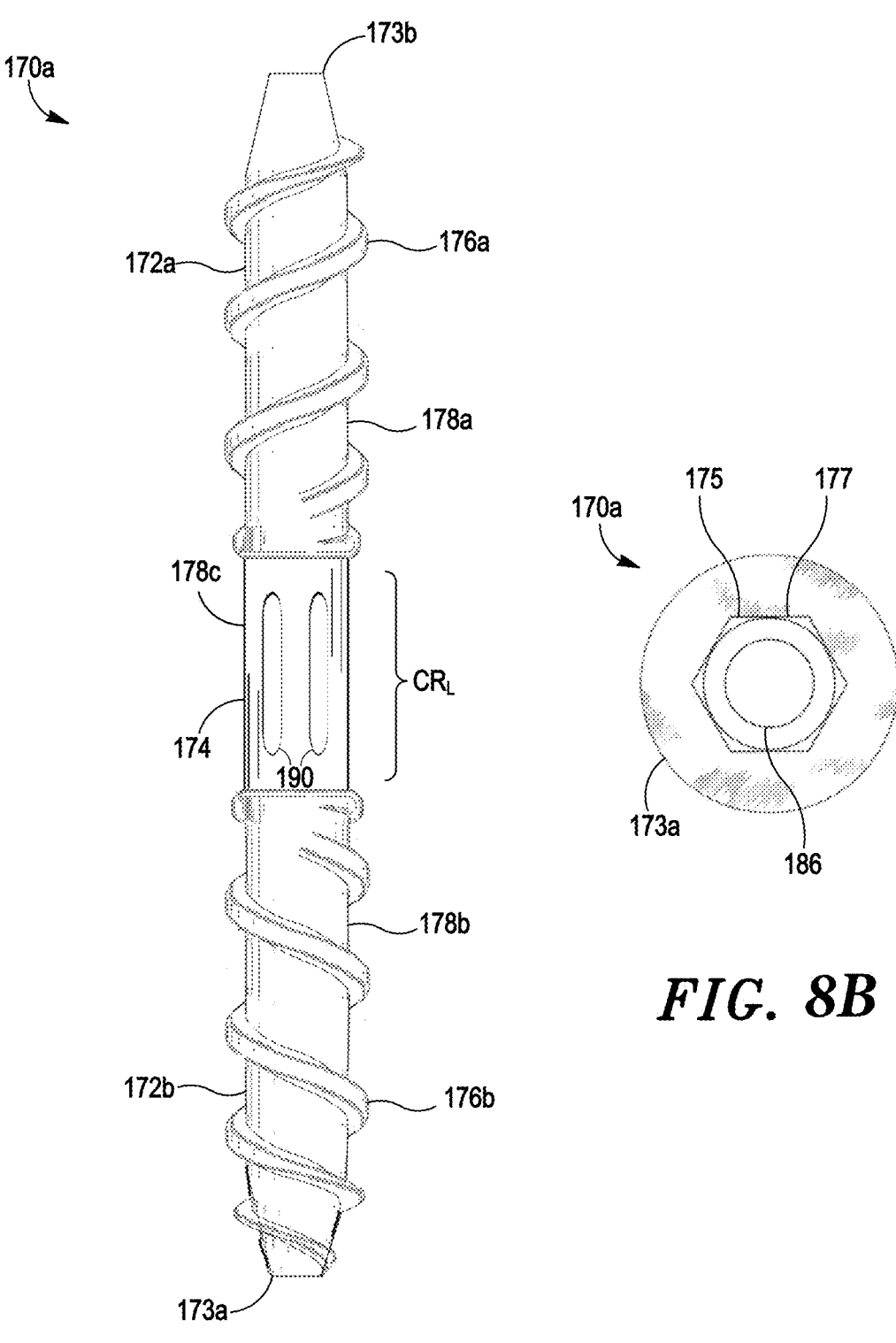
FIG. 8A is a perspective view of one embodiment of an elongated threaded prosthesis comprising dual threaded ends, in accordance with the invention.
FIG. 8B is an end plan view of the elongated threaded prosthesis shown in FIG. 8A, in accordance with the invention.

Referring first to FIG. 8A, there is shown one embodiment of a bone structure prosthesis comprising an elongated threaded member (denoted "170a").

As illustrated in FIG. 8A, the bone structure prosthesis, i.e., elongated threaded member 170a, comprises a self-tapping threaded member that is preferably adapted and configured to be inserted into and engage articular cartilage and bone structures with pilot bores or openings, such as the pilot openings discussed above. However, according to the invention, the elongated threaded member 170a can also be configured to bore into and engage articular cartilage and bone structures without a pilot opening.

According to the invention, the elongated threaded member 170a (and elongated threaded members 170b through 170i, discussed in detail below) can comprise various lengths to accommodate fixation of various dysfunctional bone structures, e.g., dysfunctional SI joints, a fractured femur, etc.

According to the invention, the non-threaded central region 174 of the elongated threaded member 170a (and elongated threaded members 170b through 170i) can also comprise various lengths (denoted "CR$_L$") to achieve a desired fixed position between bone structures (i.e., space between fixed bone structures) post-engagement and fixation with elongated threaded member 170a (and elongated threaded members 170b through 170i).

In some embodiments, the length (CR$_L$) of the non-threaded central region 174 of the elongated threaded member 170a (and elongated threaded members 170b through 170i) is less than approximately 10.0 mm.

As further illustrated in FIG. 8A, the elongated threaded member 170a comprises a first threaded end 172a, a second threaded end 172b, which is disposed opposite the first threaded end 172a, and an intervening non-threaded central region 174 disposed therebetween; the first threaded end 172a comprising a first thread 176a that preferably extends from the non-threaded central region 174 to the distal end 173b of the elongated threaded member 170a, and the second threaded end 172b comprising a second thread 176b that preferably extends from the non-threaded central region 174 to the proximal end 173a of the elongated threaded member 170a.

According to the invention, the first thread 176a can also extend any distance from the distal end 173b of the elongated threaded member 170a toward the non-threaded central region 174 thereof and, hence, can comprise various thread lengths.

According to the invention, the second thread 176b can also extend any distance from the proximal end 173a of the elongated threaded member 170a toward the non-threaded central region 174 thereof and, hence, can similarly comprise various thread lengths.

As additionally illustrated in FIG. 8A, in a preferred embodiment, the first thread 176a is disposed and positioned on the exterior surface 178a of the first threaded end 172a in a substantially helical manner, and the second thread 176b is similarly disposed and positioned on the exterior surface 178b of the second threaded end 172b in a substantially helical manner.

In a preferred embodiment, the proximal and distal ends 173a, 173b of the elongated threaded member 170a (and elongated members 170b through 170i discussed below) comprise a tapered configuration (i.e., chamfered edge) to facilitate entry of the elongated threaded member 170a (and elongated members 170b through 170i) into bone structures and/or pilot bores or openings therein.

As further illustrated in FIG. 8A, in a preferred embodiment, first and second threads 176a, 176b have reverse orientations, i.e., reverse threads, whereby, when the first and second threaded ends 172a, 172b are disposed proximate separate bone structures, such as an ilium and sacrum, or inserted into pilot openings therein, and the elongated threaded member 170a is rotated in a clockwise direction, the first and second threaded ends 172a, 172b advance into the bone structures and provide a compressive or coupling force therebetween.

According to the invention, the first and second threads 176a, 176b can also comprise various diameters, i.e., outer thread diameters and/or root or core diameters, and thread pitches to accommodate fixation of various dysfunctional bone structures.

In some embodiments, the first and/or second threads 176a, 176b of the elongated threaded member 170a comprise an outer thread diameter in the range of approximately 7.5 mm to 10.0 mm, a core diameter in the range of approximately 4.0 mm to 6.5 mm, and a thread pitch in the range of approximately 0.75 mm to 1.5 mm, i.e., a coarse thread.

In some embodiments, the first and/or second threads 176a, 176b comprise an outer thread diameter in the range of approximately 7.5 mm to 10.0 mm, a core diameter in the range of approximately 4.0 mm to 6.5 mm, and a thread pitch in the range of approximately 0.3 mm to 0.75 mm, i.e., a fine thread.

In some embodiments, the first and/or second threads 176a, 176b of the elongated threaded member 170a comprise an outer thread diameter in the range of approximately 3.5 mm to 7.0 mm, a core diameter in the range of approximately 2.0 mm to 6.0 mm, and a thread pitch in the range of approximately 0.75 mm to 1.5 mm.

In some embodiments, the first and/or second threads 176a, 176b comprise an outer thread diameter in the range of approximately 3.5 mm-7.0 mm, a core diameter in the range of approximately 2.0 mm to 6.0 mm, and a thread pitch in the range of approximately 0.3 mm to 0.75 mm.

According to the invention, to achieve optimal fixation to bone structures and osseointegration, i.e., bone or osseous tissue ingrowth into the elongated threaded member 170a, the first and second threads 176a, 176b of the elongated threaded member 170a preferably comprise a maximum thread depth, i.e., differential between the outer thread diameter and core diameter, e.g., an outer thread diameter of approximately 7.5 mm and a core diameter of approximately 4.0 mm.

In a preferred embodiment, the first and second threads 176a, 176b comprise the same thread pitch. However, according to the invention, the first and second threads 176a, 176b can also comprise different thread pitches.

Thus, in some embodiments, the first thread comprises a thread pitch in the range of approximately 0.75 mm to 1.5 mm and the second thread comprises a thread pitch in the range of approximately 0.3 mm to 0.75 mm.

In some embodiments, the first thread comprises a thread pitch in the range of approximately 0.3 mm to 0.75 mm and the second thread comprises a thread pitch in the range of approximately 0.75 mm to 1.5 mm.

In a preferred embodiment, the proximal end 173a of the elongated threaded member 170a comprises an internal insertion tool engagement region 175 that is sized and configured to receive and cooperate with an external deployment and/or extraction tool or assembly.

As illustrated in FIG. 8B, in some embodiments, the internal insertion tool engagement region 175 comprises a hex configuration or region 177 that is adapted to receive and cooperate with an external "hex" (or Allen head) deployment and/or extraction tool or assembly.

As further illustrated in FIG. 8B, in a preferred embodiment, the elongated threaded member 170a further comprises an internal region or lumen 186 that extends longitudinally through the elongated threaded member 170a from the proximal end 173a to the distal end 173b thereof.

In some embodiments of the invention, the distal end 173b of the elongated threaded member 170a comprises a closed end, whereby the internal lumen 186 of the elongated threaded member 170a is configured and adapted to receive and contain (i) agents and compositions that further facilitate adhesion of the elongated threaded member 170a to bone structures, including individual skeletal members, and articulating and non-articulating bone structures, and pilot openings therein and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 170a when the prosthesis, i.e., elongated threaded member 170a, is engaged to bone structures.

In some embodiments, the distal end 173b of the elongated threaded member 170a comprises an opened end and the internal lumen 186 of the elongated threaded member 170a is sized and configured to receive and slidably translate over a guide member.

As further illustrated in FIG. 8A, in a preferred embodiment, the non-threaded central region 174 of the elongated threaded member 170a comprises a plurality of slits 190 that extend from the exterior surface 178c of the non-threaded central region 174 to the internal lumen 186 of the elongated threaded member 170a (and, hence, are in communication with the internal lumen 186).

According to the invention, the slits 190 are sized and configured to allow agents and compositions disposed in the internal lumen 186 of the elongated threaded member 170a to be dispersed out of the internal lumen 186 and delivered to bone structures when the prosthesis, i.e., elongated threaded member 170a, is engaged thereto.

Figure 8C:
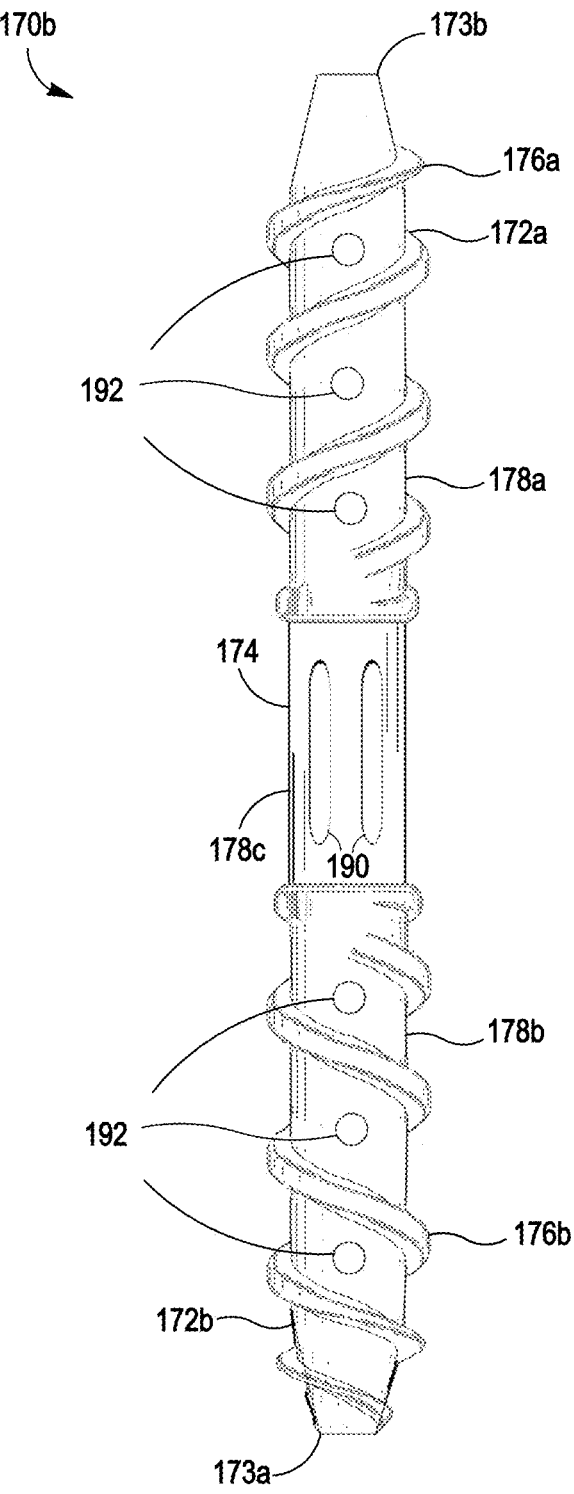

Referring now to FIG. 8C, there is shown a further embodiment of the elongated threaded member 170a shown in FIG. 8A (now denoted elongated threaded member 170b), wherein the first and second threaded ends 172a, 172b further comprise a plurality of apertures 192, which similarly extend from the exterior surfaces 178a, 178b of the first and second threaded ends 172a, 172b to the internal lumen 186 of the elongated threaded member 170b (and, hence, are in communication with the internal lumen 186), and are similarly sized and configured to allow agents and compositions disposed in the internal lumen 186 of the elongated threaded member 170b to be dispersed out of the internal lumen 186 and delivered to bone structures when the prosthesis, i.e., elongated threaded member 170b, is engaged thereto.

As indicated above, according to the invention, the elongated threaded members 170a, 170b (and elongated threaded members 170c through 170i, 270a, 270b, 370a, and 370b, discussed in detail below) can comprise various biocompatible materials, including, without limitation stainless-steel, e.g., 316L stainless steel, titanium, titanium alloys, e.g., TI-6AL-4V (including extra-low interstitial (ELI) variants thereof) and Ti-6Al-7Nb titanium alloys; cobalt-chromium alloys, e.g., ASTM F75, ASTM F799, and ASTM F1537 cobalt-chrome alloys; nickel-titanium alloys, e.g., Nitinol (55Ni-45Ti), tantalum; and magnesium ceramics, e.g., magnesium phosphates (MgO—$P_2O_5$), calcium magnesium phosphates (CaO—MgO—$P_2O_5$), and magnesium glasses (SiO$_2$—MgO).

The elongated threaded members 170a, 170b (and elongated threaded members 170c through 170i, 270a, 270b, 370a, and 370b) can also comprise various biocompatible polymers, including, without limitation, reinforced polymers, such as carbon fiber reinforced polymers and metal-framed polymers.

According to the invention, the elongated threaded members 170a, 170b (and elongated threaded members 170c through 170i, 270a, 270b, 370a, and 370b) can also comprise various biodegradable or bioabsorbable materials, including, without limitation, magnesium, magnesium-aluminum (Mg—Al) alloys, magnesium-rare earth alloys, e.g., MgYREZr and Mg-3.5Y-2.3Nd-0.5Zr (WE43) alloys; magnesium-zinc (Mg—Zn) alloys, magnesium-calcium (Mg—

Ca) alloys, e.g., Mg-5Ca-1Zn, Mg-2Sn-1Ca (TX21) and Mg-2Sn-1Ca-2Zn (TXZ212) alloys; and zinc-based alloys.

The elongated threaded members 170a, 170b (and elongated threaded members 170c through 170i, 270a, 270b, 370a, and 370b) can also comprise various composites comprising, without limitation, one of the aforementioned biodegradable polymers and/or one of the aforementioned osteogenic compositions, including, without limitation, PGS-hydroxyapatite (HA) composites, PGSA-HA composites, PLA-HA composites, etc.

The elongated threaded members 170a, 170b (and elongated threaded members 170c through 170i, 270a, 270b, 370a, and 370b) can also comprise a porous structure to facilitate osseointegration.

In some embodiments, the elongated threaded members 170a, 170b (and elongated threaded members 170c through 170i, 270a, 270b, 370a, and 370b) comprise a porosity in the range of 1% to 90%, more preferably, a porosity in the range of 30% to 85%.

In some embodiments, the elongated threaded members 170a, 170b (and elongated threaded members 170c through 170i, 270a, 270b, 370a, and 370b) comprise a pore size in the range of 100 μm to 2000 μm, more preferably, a pore size in the range of 400 μm to 600 μm.

The elongated threaded members 170a, 170b (and elongated threaded members 170c through 170i, 270a, 270b, 370a, and 370b) can also comprise various surface treatments and, hence, characteristics, e.g., roughness, such as disclosed in priority Co-pending U.S. application Ser. No. 17/469,132 to facilitate and/or support fixation of the elongated threaded members to bone structures, and further support osseointegration.

The elongated threaded members 170a, 170b (and elongated threaded members 170c through 170i, 270a, 270b, 370a, and 370b) can also comprise one of the outer coatings disclosed in priority Co-pending U.S. application Ser. No. 17/469,132, such as a poly(glycerol sebacate) (PGS)-based coating, to similarly facilitate and/or support fixation of the elongated threaded members to bone structures, and further support osseointegration.

Figures 8D, 8E:
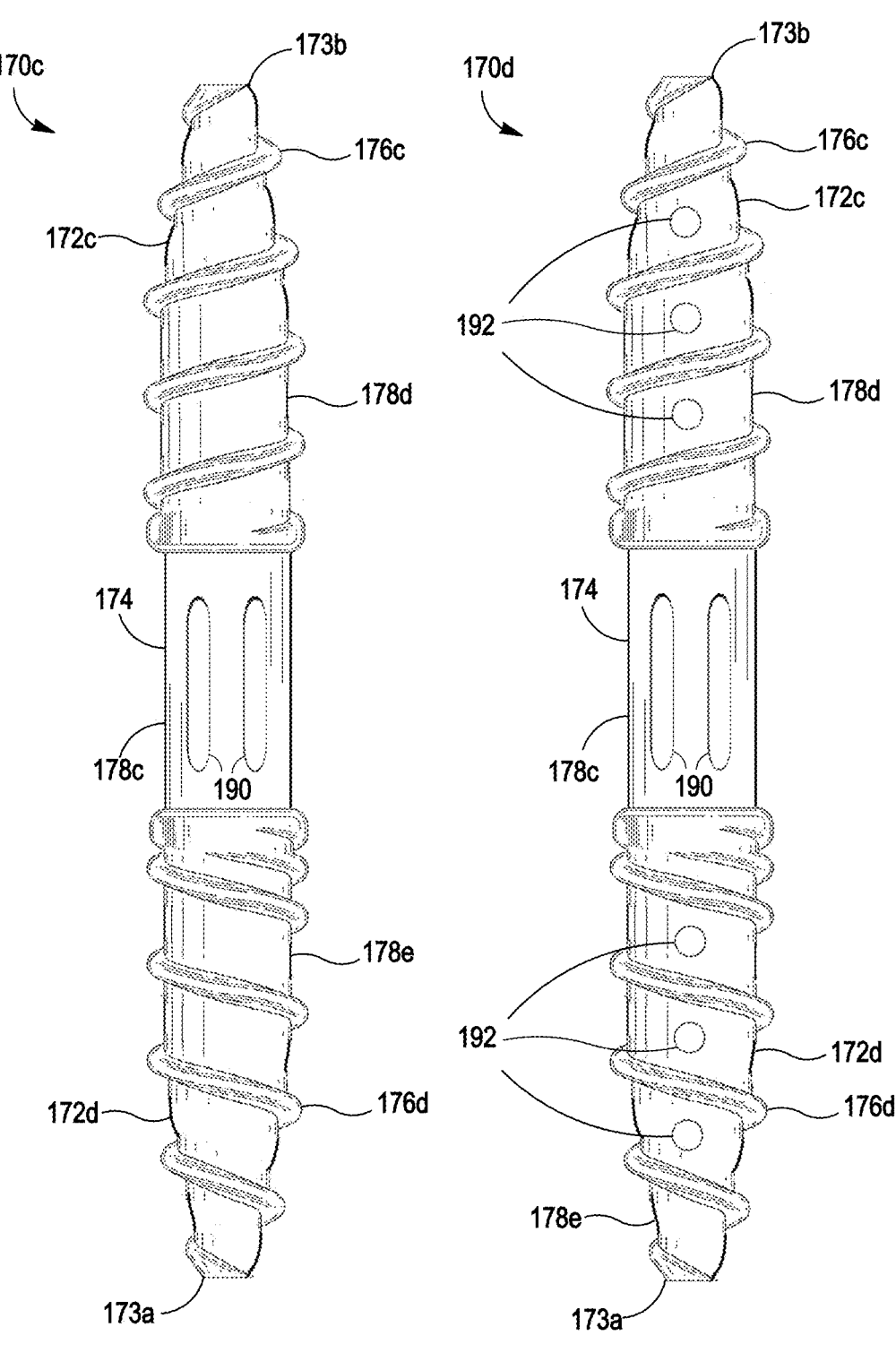

Referring now to FIG. 8D, there is shown another embodiment of the bone structure prosthesis shown in FIG. 8A (denoted "170c").

As illustrated in FIG. 8D, the bone structure prosthesis, i.e., elongated threaded member 170c, similarly comprises a self-tapping threaded member comprising a first threaded end 172c, a second threaded end 172d, and an intervening non-threaded central region 174 disposed therebetween.

However, as further illustrated in FIG. 8D, in a preferred embodiment, the first and second threaded ends 172c, 172d of the elongated threaded member 170c comprise a tapered configuration to facilitate entry of the elongated threaded member 170c into bone structures and/or pilot bores or openings therein.

As indicated above, according to the invention, the elongated threaded member 170c can comprise various lengths to accommodate fixation of various dysfunctional bone structures.

The non-threaded central region 174 of the elongated threaded member 170c can also similarly comprise various lengths to achieve a desired fixed position between bone structures (i.e., space between fixed bone structures) post-engagement and fixation with elongated threaded member 170c.

As further illustrated in FIG. 8D, in a preferred embodiment, the first threaded end 172c similarly comprises first thread 176c that preferably extends from the non-threaded central region 174 to the distal end 173b of the elongated threaded member 170c, and the second threaded end 172d comprises a second thread 176d that preferably extends from the non-threaded central region 174 to the proximal end 173a of the elongated threaded member 170c.

According to the invention, the first thread 176c can similarly also extend any distance from the distal end 173b of the elongated threaded member 170c toward the non-threaded central region 174 thereof and, hence, can comprise various thread lengths.

According to the invention, the second thread 176d can also extend any distance from the proximal end 173a of the elongated threaded member 170c toward the non-threaded central region 174 thereof and, hence, can similarly comprise various thread lengths.

In a preferred embodiment, the first thread 176c is similarly disposed and positioned on the exterior surface 178d of the first threaded end 172c in a substantially helical manner, and the second thread 176d is similarly disposed and positioned on the exterior surface 178e of the second threaded end 172d in a substantially helical manner.

As further illustrated in FIG. 8D, in a preferred embodiment, first and second threads 176c, 176d similarly comprise reverse orientations, i.e., reverse threads, whereby, as discussed above, when the first and second threaded ends 172c, 172d are disposed proximate separate bone structures, such as an ilium and sacrum, or inserted into pilot openings therein, and the elongated threaded member 170c is rotated in a clockwise direction, the first and second threaded ends 172c, 172d advance into the bone structures and provide a compressive or coupling force therebetween.

According to the invention, the elongated threaded member 170c can comprise various non-threaded central region 174 diameters, and the first and second threads 176c, 176d thereof can similarly comprise various thread depths and thread pitches to accommodate fixation of various dysfunctional bone structures.

In some embodiments, the non-threaded central region 174 of the elongated threaded member 170c comprises a diameter in the range of approximately 7.5 mm-10.0 mm.

In some embodiments, the non-threaded central region 174 of the elongated threaded member 170c comprises a diameter in the range of approximately 3.5 mm-7.0 mm.

In some embodiments, the first and/or second threads 176c, 176d of the elongated threaded member 170c comprise a thread depth in the range of approximately 2.0 mm-4.0 mm and a thread pitch in the range of approximately 0.75 mm-1.5 mm.

In some embodiments, the first and/or second threads 176c, 176d comprise a thread depth in the range of approximately 2.0 mm-4.0 mm and a thread pitch in the range of approximately 0.3 mm-0.75 mm.

According to the invention, to achieve optimal fixation to bone structures and osseointegration, the first and second threads 176c, 176d of the elongated threaded member 170c preferably comprise a maximum thread depth, e.g., approximately 4.0 mm.

In a preferred embodiment, the first and second threads 176c, 176d similarly comprise the same thread pitch. However, according to the invention, the first and second threads 176c, 176d can similarly comprise different thread pitches.

Thus, in some embodiments of the invention, the first thread 176c comprises a thread pitch of approximately 0.75 mm-1.5 mm, and the second thread comprises a thread pitch of approximately 0.3 mm-0.75 mm.

In some embodiments of the invention, the first thread 176c comprises a thread pitch of approximately 0.3 mm-0.75 mm, and the second thread comprises a thread pitch of approximately 0.75 mm-1.5 mm.

In a preferred embodiment, the proximal end 173a of the elongated threaded member 170c similarly comprises an internal insertion tool engagement region 175, such as the hex region shown in FIG. 8B above, that is sized and configured to receive and cooperate with an external deployment and/or extraction tool or assembly.

In a preferred embodiment, the elongated threaded member 170c similarly further comprises the internal region or lumen 186 that extends longitudinally through the elongated threaded member 170c from the proximal end 173a to the distal end 173b thereof.

In some embodiments of the invention, the distal end 173b of the elongated threaded member 170c similarly comprises a closed end, whereby the internal lumen 186 of the elongated threaded member 170c is similarly configured and adapted to receive and contain (i) agents and compositions that further facilitate adhesion of the elongated threaded member 170c to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 170c when the prosthesis, i.e., elongated threaded member 170c, is engaged to bone structures.

In some embodiments, the distal end 173b of the elongated threaded member 170c similarly comprises an opened end and the internal lumen 186 of the elongated threaded member 170c is similarly sized and configured to receive and slidably translate over a guide member.

As further illustrated in FIG. 8D, in a preferred embodiment, the non-threaded central region 174 of the elongated threaded member 170c similarly comprises the plurality of slits 190, which similarly extend from the exterior surface 178c of the non-threaded central region 174 to the internal lumen 186 of the elongated threaded member 170c (and, hence, are similarly in communication with the internal lumen 186), and are sized and configured to allow agents and compositions disposed in the internal lumen 186 of the elongated threaded member 170c to be dispersed out of the internal lumen 186 and delivered to bone structures when the prosthesis, i.e., elongated threaded member 170c, is engaged thereto.

Referring now to FIG. 8E, there is shown a further embodiment of the elongated threaded member 170c shown in FIG. 8D (now denoted elongated threaded member 170d), wherein the first and second threaded ends 172c, 172d of the elongated threaded member 170d similarly comprise the plurality of apertures 192, which extend from the exterior surfaces 178d, 178e of the first and second threaded ends 172c, 172d to the internal lumen 186 of the elongated threaded member 170d (and, hence, are similarly in communication with the internal lumen 186), and are similarly sized and configured to allow agents and compositions disposed in the internal lumen 186 of the elongated threaded member 170d to be dispersed out of the internal lumen 186 and delivered to bone structures when the prosthesis, i.e., elongated threaded member 170d, is engaged thereto.

Referring now to FIG. 8F, there is shown another embodiment of the bone structure prosthesis shown in FIG. 8A (denoted "170e").

As illustrated in FIG. 8F, the bone structure prosthesis, i.e., elongated threaded member 170e, similarly comprises a self-tapping threaded member comprising the first threaded end 172a, a second threaded end 172e, and an intervening non-threaded central region 174 disposed therebetween.

As further illustrated in FIG. 8F, the first threaded end 172a similarly comprises first thread 176a that preferably extends from the non-threaded central region 174 to the distal end 173b of the elongated threaded member 170a, and the second threaded end 172e comprises a second thread 176e that preferably extends from the non-threaded central region 174 to the proximal end 173a of the elongated threaded member 170e.

According to the invention, the second thread 176e can similarly extend any distance from the proximal end 173a of the elongated threaded member 170e toward the non-threaded central region 174 thereof and, hence, can similarly comprise various thread lengths.

In a preferred embodiment, the first thread 176a is similarly disposed and positioned on the exterior surface 178a of the first threaded end 172a in a substantially helical manner, and the second thread 176e is also disposed and positioned on the exterior surface 178f of the second threaded end 172e in a substantially helical manner.

However, as further illustrated in FIG. 8F, in a preferred embodiment, the first and second threads 176a, 176e have similar orientations, i.e., the first and second threads 176a, 176e wind around the exterior surfaces 178a, 178f of the first and second threaded ends 172a, 172e in the same direction.

According to the invention, the first and second threads 176a, 176e of the elongated threaded member 170e can also comprise various diameters, i.e., outer thread diameters and/or root or core diameters, and thread pitches to accommodate fixation of various dysfunctional bone structures.

In some embodiments, the first and/or second threads 176a, 176e of the elongated threaded member 170e comprise an outer thread diameter in the range of approximately 7.5 mm to 10.0 mm, a core diameter in the range of approximately 4.0 mm to 6.5 mm, and a thread pitch in the range of approximately 0.75 mm to 1.5 mm.

In some embodiments, the first and/or second threads 176a, 176e comprise an outer thread diameter in the range of approximately 7.5 mm to 10.0 mm, a core diameter in the range of approximately 4.0 mm to 6.5 mm, and a thread pitch in the range of approximately 0.3 mm to 0.75 mm.

In some embodiments, the first and/or second threads 176a, 176e of the elongated threaded member 170e comprise an outer thread diameter in the range of approximately 3.5 mm to 7.0 mm, a core diameter in the range of approximately 2.0 mm to 6.0 mm, and a thread pitch in the range of approximately 0.75 mm to 1.5 mm.

In some embodiments, the first and/or second threads 176a, 176e comprise an outer thread diameter in the range of approximately 3.5 mm to 7.0 mm, a core diameter in the range of approximately 2.0 mm to 6.0 mm, and a thread pitch in the range of approximately 0.3 mm to 0.75 mm.

According to the invention, to achieve optimal fixation to bone structures and osseointegration, i.e., bone or osseous tissue ingrowth into the elongated threaded member 170e, the first and/or second threads 176a, 176e thereof preferably similarly comprise a maximum thread depth.

In a preferred embodiment, the first and second threads 176a, 176e similarly comprise the same thread pitch. However, in some embodiments of the invention (discussed in detail below), the first and second threads 176a, 176e comprise different thread pitches.

In a preferred embodiment, the proximal end 173a of the elongated threaded member 170e similarly comprises an internal insertion tool engagement region 175, such as the hex region shown in FIG. 8B above, that is sized and configured to receive and cooperate with an external deployment and/or extraction tool or assembly.

In a preferred embodiment, the elongated threaded member 170e similarly further comprises the internal region or lumen 186 that extends longitudinally through the elongated threaded member 170e from the proximal end 173a to the distal end 173b thereof.

In some embodiments of the invention, the distal end 173b of the elongated threaded member 170e similarly comprises a closed end, whereby the internal lumen 186 of the elongated threaded member 170e is similarly configured and adapted to receive and contain (i) agents and compositions that further facilitate adhesion of the elongated threaded member 170e to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 170e when the prosthesis, i.e., elongated threaded member 170e, is engaged to bone structures.

In some embodiments, the distal end 173b of the elongated threaded member 170e similarly comprises an opened end and the internal lumen 186 of the elongated threaded member 170e is similarly sized and configured to receive and slidably translate over a guide member.

As further illustrated in FIG. 8F, in a preferred embodiment, the non-threaded central region 174 of the elongated threaded member 170e similarly comprises the plurality of slits 190, which similarly extend from the exterior surface 178c of the non-threaded central region 174 to the internal lumen 186 of the elongated threaded member 170e (and, hence, are similarly in communication with the internal lumen 186), and are sized and configured to allow agents and compositions disposed in the internal lumen 186 of the elongated threaded member 170e to be dispersed out of the internal lumen 186 and delivered to bone structures when the prosthesis, i.e., elongated threaded member 170e, is engaged thereto.

Referring now to FIG. 8G, there is shown a further embodiment of the elongated threaded member 170e shown in FIG. 8F (now denoted elongated threaded member 170f), wherein the first and second threaded ends 172a, 172e of the elongated threaded member 170f similarly comprise the plurality of apertures 192, which extend from the exterior surfaces 178a, 178f of the first and second threaded ends 172a, 172e to the internal lumen 186 of the elongated threaded member 170f (and, hence, are similarly in communication with the internal lumen 186), and are similarly sized and configured to allow agents and compositions disposed in the internal lumen 186 of the elongated threaded member 170f to be dispersed out of the internal lumen 186 and delivered to bone structures when the prosthesis, i.e., elongated threaded member 170f, is engaged thereto.

Referring now to FIG. 8H, there is shown yet embodiment of the bone structure prosthesis shown in FIG. 8F (denoted "170g").

As illustrated in FIG. 8H, the bone structure prosthesis, i.e., elongated threaded member 170g, similarly comprises a self-tapping threaded member comprising a first threaded end 172f, the second threaded end 172e, and an intervening non-threaded central region 174 disposed therebetween.

As further illustrated in FIG. 8H, the second threaded end 172e similarly comprises second thread 176e that preferably extends from the non-threaded central region 174 to the proximal end 173a of the elongated threaded member 170g, and the first threaded end 172f comprises first thread 176f that preferably extends from the non-threaded central region 174 to the distal end 173b of the elongated threaded member 170g.

According to the invention, the first thread 176f can similarly extend any distance from the distal end 173b of the elongated threaded member 170g toward the non-threaded central region 174 thereof and, hence, can similarly comprise various thread lengths.

In a preferred embodiment, the second thread 176e is similarly disposed and positioned on the exterior surface 178f of the second threaded end 172e in a substantially helical manner and the first thread 176f is also disposed and positioned on the exterior surface 178g of the first threaded end 172f in a substantially helical manner. The first and second threads 176f, 176e also have similar orientations, as the elongated threaded member 170e shown in FIG. 8F.

According to the invention, the first and second threads 176f, 176e of the elongated threaded member 170g can similarly comprise various diameters, i.e., outer thread diameters and/or root or core diameters, and thread pitches to accommodate fixation of various dysfunctional bone structures.

However, as further illustrated in FIG. 8H, in a preferred embodiment, the first and second threads 176f, 176e comprise different thread pitches, whereby, upon advancement of the elongated threaded member 170g in separate bone structures, such as the ilium and sacrum, the different thread pitches similarly provide a compressive or coupling force between the bone structures, e.g., SI joint.

Thus, in some embodiments of the invention, the first thread 176f comprises an outer thread diameter in the range of approximately 7.5 mm to 10.0 mm, a core diameter in the range of approximately 4.0 mm to 6.5 mm, and a thread pitch in the range of approximately 0.3 mm to 0.75 mm, i.e., a fine thread, and the second thread 176e comprises an outer thread diameter in the range of approximately 7.5 mm-10.0 mm, a core diameter in the range of approximately 4.0 mm to 6.5 mm, and a thread pitch in the range of approximately 0.75 mm to 1.5 mm, i.e., a coarse thread.

In the noted embodiments, such as illustrated in FIG. 8H, when the elongated threaded member 170g is engaged to separated bone structures and the elongated threaded member 170g is rotated in a clockwise direction, the bone structure engaged to the second threaded end 172e will advance further than the bone structure engaged to the first threaded end 172f, resulting in a compressive or coupling force between the bone structures.

In some embodiments of the invention, the first thread 176f comprises outer thread diameter in the range of approximately 3.5 mm to 7.0 mm, a root diameter in the range of approximately 2.0 mm to 6.0 mm, and a thread pitch in the range of approximately 0.3 mm to 0.75 mm, and the second thread 176e comprises an outer thread diameter in the range of approximately 3.5 mm to 7.0 mm, a root diameter in the range of approximately 2.0 mm to 6.0 mm, and a thread pitch in the range of approximately 0.75 mm to 1.5 mm.

In some embodiments of the invention, the first thread 176f comprises an outer thread diameter in the range of approximately 7.5 mm to 10.0 mm, a core diameter in the range of approximately 4.0 mm to 6.5 mm, and a thread pitch in the range of approximately 0.75 mm to 1.5 mm, i.e., a coarse thread, and the second thread 176e comprises an outer thread diameter in the range of approximately 7.5 mm to 10.0 mm, a core diameter in the range of approximately 4.0 mm to 6.5 mm, and a thread pitch in the range of approximately 0.3 mm to 0.75 mm, i.e., a fine thread.

In some embodiments of the invention, the first thread 176f comprises outer thread diameter in the range of approximately 3.5 mm to 7.0 mm, a root diameter in the range of approximately 2.0 mm to 6.0 mm, and a thread pitch in the range of approximately 0.75 mm to 1.5 mm, and the second thread 176e comprises an outer thread diameter in the range of approximately 3.5 mm to 7.0 mm, a root diameter in the range of approximately 2.0 mm to 6.0 mm, and a thread pitch in the range of approximately 0.3 mm to 0.75 mm.

In a preferred embodiment, the proximal end 173a of the elongated threaded member 170g similarly comprises an internal insertion tool engagement region 175, such as the hex region shown in FIG. 8B above, that is sized and configured to receive and cooperate with an external deployment and/or extraction tool or assembly.

In a preferred embodiment, the elongated threaded member 170g similarly further comprises the internal region or lumen 186 that extends longitudinally through the elongated threaded member 170g from the proximal end 173a to the distal end 173b thereof.

In some embodiments of the invention, the distal end 173b of the elongated threaded member 170g similarly comprises a closed end, whereby the internal lumen 186 of the elongated threaded member 170g is similarly configured and adapted to receive and contain (i) agents and compositions that further facilitate adhesion of the elongated threaded member 170g to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 170g when the prosthesis, i.e., elongated threaded member 170g, is engaged to bone structures.

In some embodiments, the distal end 173b of the elongated threaded member 170g similarly comprises an opened end and the internal lumen 186 of the elongated threaded member 170g is similarly sized and configured to receive and slidably translate over a guide member.

As further illustrated in FIG. 8H, in a preferred embodiment, the non-threaded central region 174 of the elongated threaded member 170g similarly comprises a plurality of slits 190, which extend from the exterior surface 178c of the non-threaded central region 174 to the internal lumen 186 of the elongated threaded member 170g (and, hence, are similarly in communication with the internal lumen 186), and are sized and configured to allow agents and compositions disposed in the internal lumen 186 of the elongated threaded member 170g to be dispersed out of the internal lumen 186 and delivered to bone structures when the prosthesis, i.e., elongated threaded member 170g, is engaged thereto.

Referring now to FIG. 8I, there is shown a further embodiment of the elongated threaded member 170g shown in FIG. 8H (now denoted elongated threaded member 170h), wherein the first and second threaded ends 172*f*, 172*e* of the elongated threaded member 170*h* similarly comprise the plurality of apertures 192, which extend from the exterior surfaces 178*g*, 178*f* of the first and second threaded ends 172*f*, 172*e* to the internal lumen 186 of the elongated threaded member 170*h* (and, hence, are similarly in communication with the internal lumen 186), and are similarly sized and configured to allow agents and compositions disposed in the internal lumen 186 of the elongated threaded member 170*h* to be dispersed out of the internal lumen 186 and delivered to bone structures when the prosthesis, i.e., elongated threaded member 170*h*, is engaged thereto.

Figure 8J:
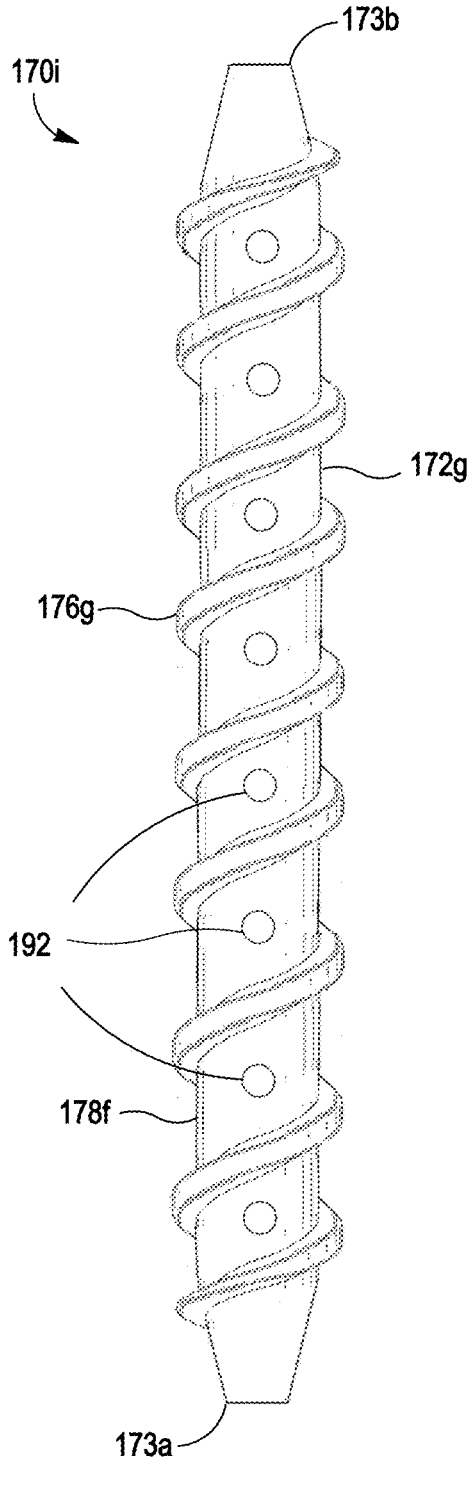

Referring now to FIG. 8J, there is shown a further embodiment of the bone structure prosthesis (denoted "170*i*").

As illustrated in FIG. 8J, the bone structure prosthesis, i.e., elongated threaded member 170*i*, similarly comprises a self-tapping threaded member comprising a threaded body 172*g*; the threaded body 172*g* comprising a thread 176*g* that extends from the proximal end 173*a* to the distal end 173*b* of the elongated threaded member 170*g*.

In a preferred embodiment, the thread 176*g* is disposed and positioned on the exterior surface 178*f* of the threaded body 172*g* in a substantially helical manner.

According to the invention, the thread 176*g* of the elongated threaded member 170*i* can also comprise various diameters, i.e., outer thread diameters and/or root or core diameters, and thread pitches to accommodate fixation of various dysfunctional bone structures.

In some embodiments, the thread 176*g* similarly comprises an outer thread diameter in the range of approximately 7.5 mm to 10.0 mm, a core diameter in the range of approximately 4.0 mm to 6.5 mm, and a thread pitch in the range of approximately 0.75 mm to 1.5 mm, i.e., a coarse thread.

In some embodiments, the thread 176*g* comprises an outer thread diameter in the range of approximately 7.5 mm to 10.0 mm, a core diameter in the range of approximately 4.0 mm to 6.5 mm, and a thread pitch in the range of approximately 0.3 mm to 0.75 mm, i.e., a fine thread.

In some embodiments, the thread 176*g* of the elongated threaded member 170*i* comprises an outer thread diameter in the range of approximately 3.5 mm to 7.0 mm, a core diameter in the range of approximately 2.0 mm to 6.0 mm, and a thread pitch in the range of approximately 0.75 mm to 1.5 mm.

In some embodiments, the thread 176*g* comprises an outer thread diameter in the range of approximately 3.5 mm to 7.0 mm, a core diameter in the range of approximately 2.0 mm to 6.0 mm, and a thread pitch in the range of approximately 0.3 mm to 0.75 mm.

According to the invention, to achieve optimal fixation to bone structures and osseointegration, i.e., bone or osseous tissue ingrowth into the elongated threaded member 170*i*, the thread 176*g* preferably similarly comprises a maximum thread depth.

In a preferred embodiment, the proximal end 173*a* of the elongated threaded member 170*i* similarly comprises an internal insertion tool engagement region 175, such as the hex region shown in FIG. 8B above, that is sized and configured to receive and cooperate with an external deployment and/or extraction tool or assembly.

In a preferred embodiment, the elongated threaded member 170*i* similarly further comprises the internal region or lumen 186 that extends longitudinally through the elongated threaded member 170*i* from the proximal end 173*a* to the distal end 173*b* thereof.

In some embodiments of the invention, the distal end 173*b* of the elongated threaded member 170*i* similarly comprises a closed end, whereby the internal lumen 186 of the elongated threaded member 170*i* is similarly configured and adapted to receive and contain (i) agents and compositions that further facilitate adhesion of the elongated threaded member 170*i* to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 170*i* when the prosthesis, i.e., elongated threaded member 170*i*, is engaged to bone structures.

In some embodiments, the distal end 173*b* of the elongated threaded member 170*i* similarly comprises an opened end and the internal lumen 186 of the elongated threaded member 170*i* is similarly sized and configured to receive and slidably translate over a guide member.

As further illustrated in FIG. 8J, in a preferred embodiment, the elongated threaded member 170*i* comprises a plurality of apertures 192, which extend from the exterior surface 178*f* of the threaded body 172*g* to the internal lumen 186 of the elongated threaded member 170*i* (and, hence, are in communication with the internal lumen 186), and are similarly sized and configured to allow agents and compositions disposed in the internal lumen 186 of the elongated threaded member 170*i* to be dispersed out of the internal lumen 186 and delivered to bone structures when the prosthesis, i.e., elongated threaded member 170*i*, is engaged thereto.

Figures 9A, 9B:
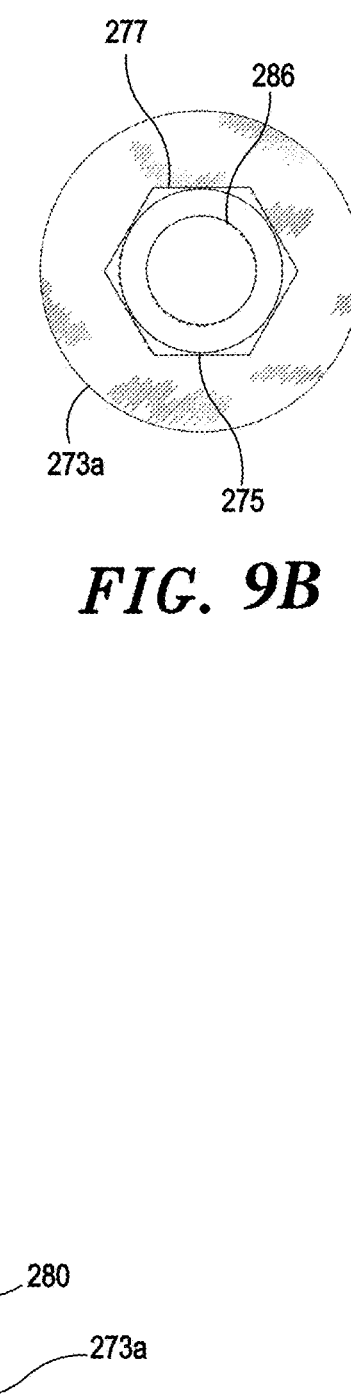
FIG. 9A is a perspective view of another embodiment of an elongated threaded prosthesis, i.e., bone structure screw, in accordance with the invention.
FIG. 9B is an end plan view of the elongated threaded prosthesis shown in FIG. 9A, in accordance with the invention.

Referring now to FIG. 9A, there is shown another embodiment of a bone structure prosthesis comprising an elongated threaded member (denoted "270*a*").

As illustrated in FIG. 9A, the bone structure prosthesis, i.e., elongated threaded member 270*a*, also comprises a self-tapping threaded member, i.e., a bone structure screw, that is preferably adapted and configured to be inserted into and engage articular cartilage and bone structures with pilot bores or openings, such as the pilot openings discussed above. However, according to the invention, the elongated threaded member 270*a* can similarly be configured to bore into and engage articular cartilage and bone structures without a pilot opening.

As indicated above, according to the invention, the elongated threaded member 270*a* (and elongated threaded members 270*b*, 370*a*, and 370*b*, discussed below) can comprise various lengths to accommodate fixation of various dysfunctional bone structures.

As indicated above, according to the invention, the elongated threaded member 270*a* (and elongated threaded members 270*b*, 370*a*, and 370*b*) can comprise various biocompatible materials, including, without limitation, stainless-steel, titanium, titanium alloys, cobalt-chromium alloys, nickel-titanium alloys, tantalum, and magnesium ceramics.

According to the invention, the elongated threaded member 270*a* (and elongated threaded members 270*b*, 370*a*, and 370*b*) can also comprise various biodegradable or bioabsorbable materials, including, without limitation, magnesium, magnesium-aluminum (Mg—Al) alloys, magnesium-rare earth alloys, magnesium-zinc (Mg—Zn) alloys, magnesium-calcium (Mg—Ca) alloys, and zinc-based alloys.

The elongated threaded member 270a (and elongated threaded members 270b, 370a, and 370b) can also comprise a porous structure to facilitate osseointegration.

The elongated threaded member 270a (and elongated threaded members 270b, 370a, and 370b) can also comprise various surface treatments and, hence, characteristics to facilitate and/or support fixation of the elongated threaded members to bone structures, and further support osseointegration.

The elongated threaded member 270a (and elongated threaded members 270b, 370a, and 370b) can also comprise an outer coating, such as disclosed in priority Co-pending U.S. application Ser. No. 17/469,132, to similarly facilitate and/or support fixation of the elongated threaded members to bone structures, and further support osseointegration.

As illustrated in FIG. 9A, the elongated threaded member 270a comprises a head region 280 and a threaded body 272a comprising a thread 276 that is disposed and positioned on the exterior surface 278a of the threaded body 272a in a substantially helical manner.

As additionally illustrated in FIG. 9A, in a preferred embodiment, the thread 276 extends from the head region 280 to the distal end 273b of the elongated threaded member 270a.

According to the invention, the thread 276 can similarly also extend any distance from the distal end 273b of the elongated threaded member 270a toward the head region 280 thereof and, hence, can comprise various thread lengths.

In a preferred embodiment, the distal end 273b of the elongated threaded member 270a (and elongated threaded member 270b) comprises a tapered end region 279 to facilitate entry of the elongated threaded member 270a (and elongated threaded member 270b) into bone structures and/ or pilot bores or openings therein.

According to the invention, the threaded body 272a of the elongated threaded member 270a can comprise various diameters, and thread 276 can similarly comprise various thread depths and thread pitches to accommodate fixation of various dysfunctional bone structures.

In some embodiments, the threaded body 272a comprises a diameter in the range of approximately 3.5 mm to 7.0 mm.

In some embodiments, the thread 276 comprises a thread depth in the range of approximately 2.0 mm to 4.0 mm and a thread pitch in the range of approximately 0.75 mm to 1.5 mm.

In some embodiments, the thread 276 comprises a thread depth in the range of approximately 2.0 mm to 4.0 mm and a thread pitch in the range of approximately 0.3 mm to 0.75 mm.

According to the invention, to achieve optimal fixation to bone structures and osseointegration, the thread 276 preferably comprises a maximum thread depth, e.g., a maximum thread depth of approximately 4.0 mm.

As further illustrated in FIG. 9A, the head region 280 of the elongated threaded member 270a (and elongated threaded member 270b) comprises a circumferential bone structure seat region 295, comprising a surface that facilitates optimal contact and engagement to articular cartilage and bone structures.

According to the invention the surface of the bone structure seat region 295 can comprise various surface features and treatments, including, without limitation, a coating comprising one of the aforementioned biodegradable adhesives or polymeric compositions, e.g., a PGS-based composition and/or a surface comprising a roughness parameter disclosed in priority Co-pending U.S. application Ser. No. 17/469,132.

As illustrated in FIGS. 9A and 9B, in a preferred embodiment, the head region 280 of the elongated threaded member 270a similarly comprises an internal insertion tool engagement region 275 that is sized and configured to receive and cooperate with an external deployment and/or extraction tool or assembly.

As further illustrated in FIGS. 9A and 9B, in some embodiments, the internal insertion tool engagement region 275 comprises a hex configuration or region 277 that is similarly adapted to receive and cooperate with an external "hex" (or Allen head) deployment and/or extraction tool or assembly.

As further illustrated in FIG. 9B, in a preferred embodiment, the elongated threaded member 270a similarly comprises an internal region or lumen 286 that extends longitudinally through the elongated threaded member 270a from the proximal end 273a to the distal end 273b (i.e., tapered end region 279) thereof.

In some embodiments of the invention, the distal end 273b of the elongated threaded member 270a similarly comprises a closed end, whereby the internal lumen 286 of the elongated threaded member 270a is similarly configured and adapted to receive and contain (i) agents and compositions that further facilitate adhesion of the elongated threaded member 270a to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 270a when the prosthesis, i.e., elongated threaded member 270a, is engaged to bone structures.

In some embodiments, the distal end 273b of the elongated threaded member 270a can similarly comprise an opened end and the internal lumen 286 of the elongated threaded member 270a is sized and configured to receive and slidably translate over a guide member.

As further illustrated in FIG. 9A, in a preferred embodiment, the threaded body 272a of the elongated threaded member 270a comprises a plurality of partially circumferential slits 290 that are in communication with the internal lumen 286 of the elongated threaded member 270a.

According to the invention, the slits 290 are similarly sized and configured to allow agents and compositions disposed in the internal lumen 286 of the elongated threaded member 270a to be dispersed out of the internal lumen 286 and delivered to bone structures when the prosthesis, i.e., elongated threaded member 270a, is engaged thereto.

Figure 9C:
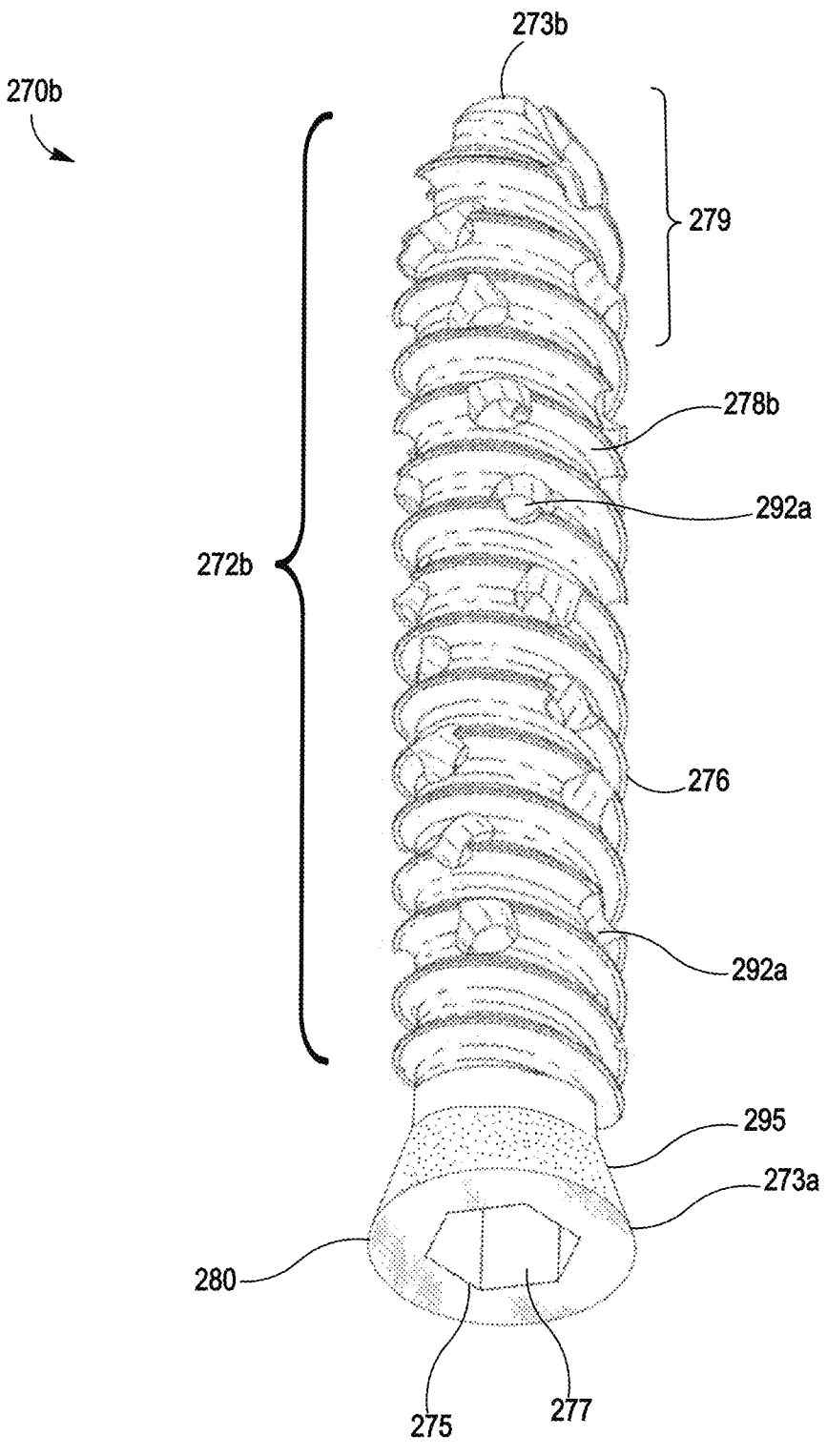
FIG. 9C is a perspective view of another embodiment of an elongated threaded prosthesis, i.e., bone structure screw, in accordance with the invention.

Referring now to FIG. 9C, there is shown a further embodiment of the elongated threaded member 270a shown in FIG. 9A (now denoted elongated threaded member 270b), wherein the threaded body 272b alternatively comprises a plurality of apertures 292a, which similarly extend from the exterior surface 278b of the threaded end 272b to the internal lumen 286 of the elongated threaded member 270b (and, hence, are in communication with the internal lumen 286), and are similarly sized and configured to allow agents and compositions disposed in the internal lumen 286 of the elongated threaded member 270b to be dispersed out of the internal lumen 286 and delivered to bone structures when the prosthesis, i.e., elongated threaded member 270b, is engaged thereto.

Referring now to FIG. 10A, there is shown another embodiment of a bone structure prosthesis comprising an elongated threaded member (denoted "370*a*").

As illustrated in FIG. 10A, the bone structure prosthesis, i.e., elongated threaded member 370*a*, also comprises a self-tapping threaded member that is preferably adapted and configured to be inserted into and engage articular cartilage and bone structures with pilot bores or openings, such as the pilot openings discussed above. However, according to the invention, the elongated threaded member 370*a* can similarly be configured to bore into and engage articular cartilage and bone structures without a pilot opening.

As further illustrated in FIG. 10A, the elongated threaded member 370*a* similarly comprises a head region 380 and a threaded body 372*a* comprising a thread 376 that is disposed and positioned on the exterior surface 378*a* of the threaded body 372*a* in a substantially helical manner.

As additionally illustrated in FIG. 10A, in a preferred embodiment, the thread 376 extends from the head region 380 (and, hence, proximal end 375*a* of the threaded body 372*a*) to the distal end 373*b* of the elongated threaded member 370*a* (and, hence, distal end 375*b* of the threaded body 372*a*).

According to the invention, the thread 376 can similarly also extend any distance from the head region 380 (and, hence, proximal end 375*a* of the threaded body 372*a*) of the elongated threaded member 370*a* toward the distal end 373*b* (and, hence, distal end 375*b* of the threaded body 372*a*) thereof and, hence, can comprise various thread lengths.

In a preferred embodiment, the threaded body 372*a* of the elongated threaded member 370*a* (and threaded body 372*b* of the elongated threaded member 370*b*, discussed below) comprises a tapered configuration to facilitate entry of the elongated threaded member 370*a* (and elongated threaded member 370*b*) into bone structures and/or pilot bores or openings therein.

According to the invention, the head region 380 and, hence, proximal end 375*a* of the threaded body 372*a* of the elongated threaded member 370*a* can comprise various diameters, and thread 376 can similarly comprise various thread depths and thread pitches to accommodate fixation of various dysfunctional bone structures.

In some embodiments, the head region 380 and, hence, proximal end 375*a* of the threaded body 372*a* of the elongated threaded member 370*a* comprise a diameter in the range of approximately 3.5 mm to 7.0 mm.

In some embodiments, the thread 376 comprises a thread depth in the range of approximately 2.0 mm to 4.0 mm and a thread pitch in the range of approximately 0.75 mm to 1.5 mm.

In some embodiments, the thread 376 comprises a thread depth in the range of approximately 2.0 mm to 4.0 mm and a thread pitch in the range of approximately 0.3 mm to 0.75 mm.

According to the invention, to achieve optimal fixation to bone structures and osseointegration, the thread 376 preferably comprises a maximum thread depth, e.g., a maximum thread depth of approximately 4.0 mm.

As illustrated in FIGS. 10A and 10B, in a preferred embodiment, the head region 380 of the elongated threaded member 370*a* similarly comprises an internal insertion tool engagement region 375 that is sized and configured to receive and cooperate with an external deployment and/or extraction tool or assembly.

As further illustrated in FIGS. 10A and 10B, in some embodiments, the internal insertion tool engagement region 375 comprises a hex configuration or region 377 that is similarly adapted to receive and cooperate with an external "hex" (or Allen head) deployment and/or extraction tool or assembly.

As further illustrated in FIG. 10B, in a preferred embodiment, the elongated threaded member 370*a* similarly comprises an internal region or lumen 386 that extends longitudinally through the elongated threaded member 370*a* from the proximal end 373*a* to the distal end 373*b* thereof.

In some embodiments of the invention, the distal end 373*b* of the elongated threaded member 370*a* similarly comprises a closed end, whereby the internal lumen 386 of the elongated threaded member 370*a* is similarly configured and adapted to receive and contain (i) agents and compositions that further facilitate adhesion of the elongated threaded member 370*a* to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated threaded member 370*a* when the prosthesis, i.e., elongated threaded member 370*a*, is engaged to bone structures.

In some embodiments, the distal end 373*b* of the elongated threaded member 370*a* can similarly comprise an opened end and the internal lumen 386 of the elongated threaded member 370*a* is sized and configured to receive and slidably translate over a guide member.

As further illustrated in FIG. 10A, in a preferred embodiment, the elongated threaded member 370*a* comprises a partially circumferential non-threaded or relief portion 393 disposed along the exterior surface 378*a* of the threaded body 372*a* that is configured and adapted to facilitate and/or support fixation of the elongated threaded member 370*a* to bone structures, and further support osseointegration.

Referring now to FIG. 10C, there is shown a further embodiment of the elongated threaded member 370*a* shown in FIG. 10A (now denoted elongated threaded member 370*b*), wherein the threaded body 372*b* further comprises a plurality of apertures 392, which similarly extend from the exterior surface 378*b* of the threaded end 372*b* to the internal lumen 386 of the elongated threaded member 370*b* (and, hence, are in communication with the internal lumen 386), and are similarly sized and configured to allow agents and compositions disposed in the internal lumen 386 of the elongated threaded member 370*b* to be dispersed out of the internal lumen 386 and delivered to bone structures when the prosthesis, i.e., elongated threaded member 370*b*, is engaged thereto.

Referring now to FIGS. 11A-11H, 12A-12C, and 13A-13B, various embodiments of bone structure prostheses comprising elongated non-threaded members will be described in detail.

According to the invention, the bone structure prostheses, i.e., elongated non-threaded members, are adapted and configured to be inserted into and engage pilot bores or openings in bone structures, such as the pilot openings discussed above. In a preferred embodiment of the invention, the elongated non-threaded members are configured and adapted to be interference-fit or press-fit into pilot bores or openings.

Referring now to FIG. 11A, there is shown one embodiment of a bone structure prosthesis, i.e., elongated non-threaded member, of the invention (denoted "470*a*").

As illustrated in FIG. 11A, the elongated non-threaded member 470a comprises a first end 472a, a second end 472b, which is disposed opposite the first end 472a, and an intervening central region 474 disposed therebetween.

According to the invention, the elongated non-threaded member 470a (and elongated non-threaded members 470b and 470c, discussed in detail below) can similarly comprise various lengths to accommodate fixation of various dysfunctional bone structures, e.g., dysfunctional SI joints, a fractured femur, etc.

In a preferred embodiment, the proximal and distal ends 473a, 473b of the elongated non-threaded member 470a (and elongated non-threaded members 470b and 470c) comprise a tapered configuration (i.e., chamfered edge) to facilitate entry of the elongated non-threaded member 470a (and elongated non-threaded members 470b and 470c) into pilot bores or openings in bone structures.

According to the invention, the first and second ends 472a, 472b of the elongated non-threaded member 470a (and elongated non-threaded members 470b and 470c) can also comprise various diameters to accommodate fixation of various dysfunctional bone structures.

In some embodiments, the first and second ends 472a, 472b of the elongated non-threaded member 470a (and elongated non-threaded members 470b and 470c) comprise an exterior diameter in the range of 7.5 mm-10.0 mm.

In some embodiments, the first and second ends 472a, 472b of the elongated non-threaded member 470a (and elongated non-threaded members 470b and 470c) comprise an exterior diameter in the range of 3.5-7.0 mm.

In a preferred embodiment of the invention, the first and second ends 472a, 472b of the elongated non-threaded member 470a (and/or elongated non-threaded members 470b and 470c) comprise substantially similar exterior diameters. However, according to the invention, the first and second ends 472a, 472b of the elongated non-threaded member 470a (and/or elongated non-threaded members 470b and 470c) can comprise different exterior diameters.

According to the invention, the elongated non-threaded member 470a (and elongated non-threaded members 470b and 470c) can comprise any suitable cross-sectional shape. Referring to FIGS. 11D through 11H, exemplar suitable cross-sectional shapes include a circular or cylindrical cross-sectional shape, such as shown in FIG. 11D, a substantially rectangular cross-sectional shape or substantially square cross-sectional shape, such as shown in FIG. 11E, a substantially triangular cross-sectional shape, such as shown in FIGS. 11F and 11H, and a substantially hexagonal cross-sectional shape, such as shown in FIG. 11G.

In a preferred embodiment, the proximal end 473a of the elongated non-threaded member 470a (and elongated non-threaded members 470b and 470c) similarly comprises an internal insertion tool engagement region 475 that is sized and configured to receive and cooperate with an external deployment and/or extraction tool or assembly.

As illustrated in FIGS. 11D-11H, in some embodiments, the internal insertion tool engagement region 475 comprises a hex configuration or region 477 that is adapted to receive and cooperate with an external "hex" (or Allen head) deployment and/or extraction tool or assembly.

As further illustrated in FIG. 11A and FIGS. 11D-11H, in a preferred embodiment, the elongated non-threaded member 470a further comprises an internal region or lumen 486 that extends longitudinally through the elongated non-threaded member 470a from the proximal end 473a to the distal end 473b thereof.

In some embodiments of the invention, the distal end 473b of the elongated non-threaded member 470a (and elongated non-threaded members 470b and 470c) comprises a closed end, whereby the internal lumen 486 of the elongated non-threaded member 470a (and elongated non-threaded members 470b and 470c) is configured and adapted to receive and contain (i) agents and compositions that further facilitate adhesion of the elongated non-threaded member 470a to bone structures, including individual skeletal members, and articulating and non-articulating bone structures, and pilot openings therein and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated non-threaded member 470a when the elongated non-threaded member 470a, and elongated non-threaded members 470b and 470c, are engaged to bone structures.

In some embodiments, the distal end 473b of the elongated non-threaded member 470a (and elongated non-threaded members 470b and 470c) comprises an opened end and the internal lumen 486 of the elongated non-threaded member 470a (and elongated non-threaded members 470b and 470c) is sized and configured to receive and slidably translate over a guide member.

As illustrated in FIG. 11A, in a preferred embodiment, the central region 474 of the elongated non-threaded member 470a (and elongated non-threaded members 470b and 470c) comprises a plurality of slits 490 that extend from the exterior surface 478c of the central region 474 to the internal lumen 486 (and, hence, are similarly in communication with the internal lumen 486).

According to the invention, the slits 490 are sized and configured to allow agents and compositions disposed in the internal lumen 486 of the elongated non-threaded member 470a (and elongated non-threaded members 470b and 470c) to be dispersed out of the internal lumen 486 and delivered to bone structures when the elongated non-threaded member 470a, and elongated non-threaded members 470b and 470c, are engaged to bone structures.

As further illustrated in FIG. 11A, the first and second ends 472a, 472b of the elongated non-threaded member 470a also comprise a plurality of apertures 492a, which extend from the exterior surfaces 478a, 478b of the first and second ends 472a, 472b to the internal lumen 486 of the elongated non-threaded member 470a (and, hence, are similarly in communication with the internal lumen 486), and are similarly sized and configured to allow agents and compositions disposed in the internal lumen 486 of the elongated non-threaded member 470a to be dispersed out of the internal lumen 486 and delivered to bone structures when the prosthesis, i.e., elongated non-threaded member 470a, is engaged thereto.

Referring now to FIG. 11B, there is shown a further embodiment of the elongated non-threaded member 470a shown in FIG. 11A (now denoted elongated non-threaded member 470b), wherein the first and second ends 472a, 472b of the elongated non-threaded member 470a similarly comprise a plurality of apertures 492b, which similarly extend from the exterior surfaces 478a, 478b of the first and second ends 472a, 472b to the internal lumen 486 of the elongated non-threaded member 470a (and, hence, are in communication with the internal lumen 486), and are similarly sized and configured to allow agents and compositions disposed in the internal lumen 486 of the elongated non-threaded member 470*b* to be dispersed out of the internal lumen 486 and delivered to bone structures when the prosthesis, i.e., elongated non-threaded member 470*b*, is engaged thereto.

However, as illustrated in FIG. 11B, the plurality of apertures 492*b*, in this instance, comprise diagonally oriented, partially circumferential apertures.

Referring now to FIG. 11C, there is shown yet another embodiment of the elongated non-threaded member 470*a* shown in FIG. 11A (now denoted elongated non-threaded member 470*c*), wherein the first and second ends 472*a*, 472*b* of the elongated non-threaded member 470*a* also comprise a plurality of apertures 492*c*, which similarly extend from the exterior surfaces 478*a*, 478*b* of the first and second ends 472*a*, 472*b* to the internal lumen 486 of the elongated non-threaded member 470*c* (and, hence, are in communication with the internal lumen 486), and are similarly sized and configured to allow agents and compositions disposed in the internal lumen 486 of the elongated non-threaded member 470*c* to be dispersed out of the internal lumen 486 and delivered to bone structures when the prosthesis, i.e., elongated non-threaded member 470*c*, is engaged thereto.

As illustrated in FIG. 11B, the plurality of apertures 492*c*, in this instance, comprise horizontally oriented, partially circumferential apertures.

Referring now to FIGS. 12A and 12B, there is shown another embodiment of an elongated non-threaded member (denoted "570").

As illustrated in FIGS. 12A and 12B, in a preferred embodiment, the distal end 573*b* of the elongated non-threaded member 570 comprises a tapered end region 579 to facilitate entry of the elongated non-threaded member 570 into pilot bores or openings in bone structures.

According to the invention, the elongated non-threaded member 570 (and elongated non-threaded members 670*a* and 670*b*) can similarly comprise various lengths to accommodate fixation of various dysfunctional bone structures, e.g., dysfunctional SI joints, a fractured femur, etc.

According to the invention, the elongated non-threaded member 570 (and elongated non-threaded members 670*a* and 670*b*) can similarly also comprise various diameters to accommodate fixation of various dysfunctional bone structures.

In some embodiments, the elongated non-threaded member 570 (and elongated non-threaded members 670*a* and 670*b*) comprise an exterior diameter in the range of 7.5 mm-10.0 mm.

In some embodiments, the elongated non-threaded member 570 (and elongated non-threaded members 670*a* and 670*b*) comprise an exterior diameter in the range of 3.5-7.0 mm.

As illustrated in FIG. 12C, in a preferred embodiment, the elongated non-threaded member 570 similarly comprises an internal region or lumen 586 that extends longitudinally through the elongated non-threaded member 570 from the proximal end 573*a* to the distal end 573*b* (i.e., tapered end region 579) thereof.

In some embodiments of the invention, the distal end 573*b* of the elongated non-threaded member 570 similarly comprises a closed end, whereby the internal lumen 586 of the elongated non-threaded member 570 is similarly configured and adapted to receive and contain (i) agents and compositions that further facilitate adhesion of the elongated non-threaded member 570 to bone structures, including individual skeletal members, and articulating and non-articulating bone structures, and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated non-threaded member 570 when the prosthesis, i.e., elongated non-threaded member 570, is engaged to bone structures.

In some embodiments, the distal end 573*b* of the elongated non-threaded member 570 can similarly comprise an opened end and the internal lumen 586 of the elongated non-threaded member 570 is sized and configured to receive and slidably translate over a guide member.

As further illustrated in FIGS. 12A and 12B, in a preferred embodiment, the elongated non-threaded member 570 comprises a plurality of partially circumferential openings or apertures 592, which extend from the exterior surface 578 of the elongated non-threaded member 570 to the internal lumen 586 of the elongated non-threaded member 570 (and, hence, are in communication with the internal lumen 586), and are similarly sized and configured to allow agents and compositions disposed in the internal lumen 586 of the elongated non-threaded member 570 to be dispersed out of the internal lumen 586 and delivered to bone structures when the prosthesis, i.e., elongated non-threaded member 570, is engaged thereto.

As further illustrated in FIG. 12C, in a preferred embodiment, the proximal end 573*a* of the elongated non-threaded member 570 similarly comprises an internal insertion tool engagement region 575 that is similarly sized and configured to receive and cooperate with an external deployment and/or extraction tool or assembly.

As further illustrated in FIG. 12C, in some embodiments, the internal insertion tool engagement region 575 similarly comprises a hex configuration or region 577 that is similarly adapted to receive and cooperate with an external "hex" (or Allen head) deployment and/or extraction tool or assembly.

Referring now to FIGS. 13A and 13B, there is shown further embodiments of an elongated non-threaded member (denoted "670*a*" and "670*b*").

As illustrated in FIGS. 13A and 13B, the elongated non-threaded members 670*a*, 670*b* similarly comprise proximal and distal ends 673*a*, 673*b*.

According to the invention, the elongated non-threaded members 670*a*, 670*b* similarly comprise an internal region or lumen 686 that extends longitudinally through the elongated non-threaded members 670*a*, 670*b* from the proximal end 673*a* to the distal end 673*b* thereof (see FIG. 13B).

In a preferred embodiment of the invention, the distal end 673*b* of the elongated non-threaded members 670*a*, 670*b* similarly comprises a closed end, whereby the internal lumen 686 of the elongated non-threaded members 670*a*, 670*b* is similarly configured and adapted to receive and contain (i) agents and compositions that further facilitate adhesion of the elongated non-threaded members 670*a*, 670*b* to bone structures and pilot openings therein, and/or (ii) one or more of the aforementioned biologically active agents and compositions, including osteogenic agents and compositions, and pharmacological agents and compositions that promote or induce cell proliferation, and/or growth and/or remodeling and/or regeneration of osseous tissue, i.e., healing of osseous tissue, and/or facilitate osseous tissue ingrowth into the elongated non-threaded members 670*a*, 670*b* when engaged to bone structures.

In some embodiments, the distal end 673*b* of the elongated non-threaded members 670*a*, 670*b* can similarly comprise an opened end and the internal lumen 686 is sized and configured to receive and slidably translate over a guide member.

As further illustrated in FIG. 13A, in a preferred embodiment, the elongated non-threaded members 670a, 670b further comprise a plurality of apertures 692, which extend from the exterior surfaces 678a, 678b of the elongated non-threaded members 670a, 670b to the internal lumen 686 of the elongated non-threaded members 670a, 670b (and, hence, are in communication with the internal lumen 686), and are similarly sized and configured to allow agents and compositions disposed in the internal lumen 686 of the elongated non-threaded members 670a, 670b to be dispersed out of the internal lumen 686 and delivered to bone structures when the prostheses, i.e., elongated non-threaded members 670a, 670b, are engaged thereto.

As illustrated in FIG. 13B, in a preferred embodiment, the proximal end 673a of the elongated non-threaded members 670a, 670b similarly comprise an internal insertion tool engagement region 675 that is similarly sized and configured to receive and cooperate with an external deployment and/or extraction tool or assembly.

In some embodiments, the internal insertion tool engagement region 675 similarly comprises a hex configuration or region that is similarly adapted to receive and cooperate with an external "hex" (or Allen head) deployment and/or extraction tool or assembly.

According to the invention, the elongated non-threaded members 670a, 670b can comprise a substantially smooth surface, such as exterior surface 678a of elongated non-threaded member 670a, or any suitable surface feature(s), such as the finned exterior surface 678b of elongated non-threaded member 670b.

As indicated above, according to the invention, the elongated non-threaded members 470a, 470b, 470c, 570, 670a, and 670b can similarly comprise various biocompatible materials, including, without limitation stainless-steel, titanium, titanium alloys, cobalt-chromium alloys, nickel-titanium alloys, e.g., Nitinol (55Ni-45Ti), tantalum, and magnesium ceramics.

The elongated non-threaded members 470a, 470b, 470c, 570, 670a, and 670b can also comprise various biocompatible polymers, including, without limitation, reinforced polymers, such as carbon fiber reinforced polymers and metal-framed polymers.

The elongated non-threaded members 470a, 470b, 470c, 570, 670a, and 670b can similarly comprise various biodegradable or bioabsorbable materials, including, without limitation, magnesium, magnesium-aluminum (Mg—Al) alloys, magnesium-rare earth alloys, magnesium-zinc (Mg—Zn) alloys, magnesium-calcium (Mg—Ca) alloys, and zinc-based alloys.

The elongated non-threaded members 470a, 470b, 470c, 570, 670a, and 670b can also similarly comprise various composites comprising, without limitation, one of the aforementioned biodegradable polymers and/or one of the aforementioned osteogenic compositions, including, without limitation, PGS-hydroxyapatite (HA) composites, PGSA-HA composites, PLA-HA composites, etc.

The elongated non-threaded members 470a, 470b, 470c, 570, 670a, and 670b can also similarly comprise a porous structure to facilitate osseointegration.

The elongated non-threaded members 470a, 470b, 470c, 570, 670a, and 670b can also comprise various outer coatings.

According to the invention, the outer coating(s) can comprise (i) one of the aforementioned biocompatible and, preferably, biodegradable adhesive compositions, (ii) one of the aforementioned biologically active or pharmacological compositions, and/or (iii) one of the aforementioned polymer compositions.

According to the invention, there is thus also provided methods for stabilizing dysfunctional skeletal members, e.g., fractured bones, and dysfunctional bone structures, such as dysfunctional SI joints, comprising (i) providing a suitable prosthesis of the invention, (ii) creating a pilot opening in the dysfunctional skeletal member or bone structure, if necessary, and (iii) delivering the prosthesis to the dysfunctional skeletal member or bone structure.

As will readily be appreciated by one having ordinary skill in the art, the present invention provides numerous advantages compared to prior art methods and apparatus for stabilizing bone structures. Among the advantages are the following:

the provision of improved bone structure stabilization methods and prostheses, which can be readily employed to stabilize dysfunctional bone structures, including individual skeletal members and non-articulating and articulating bone structures; particularly, dysfunctional SI and intervertebral joints;

the provision of improved bone structure prostheses, which, when implanted in a dysfunctional non-articulating or articulating bone structure, such as a dysfunctional SI or intervertebral joint, effectively ameliorate pain associated with bone structure dysfunction; the provision of improved bone structure prostheses that can readily be employed in minimally-invasive bone structure stabilization methods and provide secure engagement to bone structures;

the provision of improved bone structure prostheses that possess optimal structural properties;

the provision of improved bone structure prostheses that can be readily employed to stabilize individual bone structures, i.e., skeletal members, via fixation or fusion; and the provision of improved bone structure prostheses that facilitate remodeling of damaged osseous tissue and regeneration of new osseous tissue and osseous tissue structures when engaged to bone structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for stabilizing a dysfunctional bone structure of a subject, comprising the steps of:

providing a bone structure prosthesis, said bone structure prosthesis comprising an elongated threaded member adapted to threadably engage bone structures, said elongated threaded member comprising a monolithic structure, said elongated threaded member further comprising a first self-tapping threaded end region, a second self-tapping threaded end region, and an intervening non-threaded central region that is disposed between said first self-tapping threaded end region and said second self-tapping threaded end region, said elongated threaded member further comprising a proximal tapered end region and a distal tapered end region, said distal tapered end region comprising a closed configuration, said first self-tapping threaded end region comprising a first proximal end and a first distal end, said first self-tapping threaded end region further comprising a first helical thread, said first helical thread extending from said first distal end to said first proximal end of said first self-tapping threaded end region in a first direction, said second self-tapping threaded end region comprising a second proximal end and a second distal end, said second self-tapping threaded end region comprising a second helical thread, said second helical thread extending from said second proximal end to said second distal end of said second self-tapping threaded end region in a second direction, said first direction of said first helical thread being opposite said second direction of said second helical thread, wherein said first helical thread and said second helical thread comprise reverse orientations, whereby, when said dysfunctional bone structure comprises a first bone segment and a second bone segment, said first self-tapping threaded end region of said elongated threaded member is inserted into said first bone segment, said second self-tapping threaded end region of said elongated threaded member is inserted into said second bone segment, and said elongated threaded member is rotated in a first direction, said first self-tapping threaded end region advances into said first bone segment and said second self-tapping threaded end region advances into said second bone segment, wherein said first and second self-tapping threaded end regions jointly provide a coupling force between said first and second bone segments, said elongated threaded member further comprising an internal lumen that extends longitudinally through said elongated threaded member from said proximal tapered end region to said distal tapered end region of said elongated threaded member, said elongated threaded member further comprising an osteogenic composition, said osteogenic composition disposed in said internal lumen, said non-threaded central region of said elongated threaded member comprising a plurality of slits that extends from a first exterior surface of said non-threaded central region to said internal lumen, said plurality of slits adapted to allow said osteogenic composition to be dispersed out of said internal lumen and into and though said plurality of slits, and delivered to said dysfunctional bone structure when said elongated threaded member is engaged thereto, said first self-tapping threaded end region of said elongated threaded member comprising a first plurality of apertures in communication with said internal lumen, said first plurality of apertures configured and adapted to allow said osteogenic composition to be dispersed out of said internal lumen and into and through said first plurality of apertures, and delivered to said dysfunctional bone structure when said elongated threaded member is threadably engaged thereto, said second self-tapping threaded end region of said elongated threaded member comprising a second plurality of apertures in communication with said internal lumen, said second plurality of apertures configured and adapted to allow said osteogenic composition to be dispersed out of said internal lumen and into and through said second plurality of apertures, and delivered to said dysfunctional bone structure when said elongated threaded member is threadably engaged thereto;

positioning said elongated threaded member between said first and second bone segments of said dysfunctional bone structure, wherein said proximal tapered end region of said elongated threaded member is in contact with said first bone segment of said dysfunctional bone structure and said distal tapered end region of said elongated threaded member is in contact with said second bone segment of said dysfunctional bone structure; and rotating said elongated threaded member in said first direction, wherein said first self-tapping threaded end region of said elongated threaded member advances into said first bone segment and said second self-tapping threaded end region of said elongated threaded member advances into said second bone segment, whereby said first and second self-tapping threaded end regions said jointly provide said coupling force between said first and second bone segments.

2. The method of claim 1, wherein said osteogenic composition comprises a bone morphogenic protein (BMP) selected from the group consisting of BMP-1, BMP2a, BMP2b, BMP3, BMP4, BMP5, BMP6, BMP7, and BMP8a.

3. The method of claim 1, wherein said osteogenic composition comprises an antibiotic selected from the group consisting of penicillin, a carboxypenicillin, a tetracycline, gentamicin, vancomycin, ciprofloxacin, amikacin, an aminoglycoside, a cephalosporin, clindamycin, erythromycin, a fluoroquinolone, a macrolide, an azolide, metronidazole, trimethoprim-sulfamethoxazole, polymyxin B, oxytetracycline, tobramycin, cefazolin, and rifampin.

4. The method of claim 1, wherein said osteogenic composition comprises an anti-inflammatory selected from the group consisting of dexamethasone, betamethasone, prednisone, prednisolone, methylprednisolone sodium succinate, methylprednisolone, cortisone, ketorolac, diclofenac, and ibuprofen.

5. The method of claim 1, wherein said osteogenic composition comprises a biologically active agent.

6. The method of claim 5, wherein said biologically active agent comprises a cell selected from the group consisting of a human embryonic stem cell, mesenchymal stem cell, hematopoietic stem cell, bone marrow-derived progenitor cell, bone marrow stromal cell (BMSCs), osteoprogenitor cell, osteoblast, osteocyte, and osteoclast.

7. The method of claim 5, wherein said biologically active agent comprises a growth factor selected from the group consisting of a transforming growth factor-alpha (TGF-$\alpha$), transforming growth factor-beta (TGF-$\beta$), fibroblast growth factor-2 (FGF-2), and vascular endothelial growth factor (VEGF).

8. The method of claim 1, wherein said elongated threaded member comprises a biodegradable material selected from the group consisting of magnesium, a magnesium-aluminum (Mg—Al) alloy, magnesium-rare earth alloy, magnesium-zinc (Mg—Zn) alloy, magnesium-calcium (Mg—Ca) alloy, and zinc-based alloy.

9. The method of claim 1, wherein said elongated threaded member comprises an outer coating.

10. The method of claim 9, wherein said outer coating comprises a poly(glycerol sebacate) (PGS)-based coating.

* * * * *